United States Patent
Kato et al.

(10) Patent No.: US 11,888,080 B2
(45) Date of Patent: Jan. 30, 2024

(54) DETECTION DEVICE INCLUDING LIGHT SOURCES ALONG AN OUTER CIRCUMFERENCE OF TWO DETECTION AREAS EACH OF THE DETECTION AREAS HAVING A SPECIFIC SCAN DIRECTION

(71) Applicants: Japan Display Inc., Tokyo (JP); The University of Tokyo, Tokyo (JP)

(72) Inventors: Hirofumi Kato, Tokyo (JP); Takanori Tsunashima, Tokyo (JP); Makoto Uchida, Tokyo (JP); Takashi Nakamura, Tokyo (JP); Akio Takimoto, Tokyo (JP); Takao Someya, Tokyo (JP); Tomoyuki Yokota, Tokyo (JP)

(73) Assignee: Japan Display Inc., Tokyo (JP)

( * ) Notice: Subject to any disclaimer, the term of this patent is extended or adjusted under 35 U.S.C. 154(b) by 73 days.

(21) Appl. No.: 17/358,950

(22) Filed: Jun. 25, 2021

(65) Prior Publication Data

US 2021/0326623 A1  Oct. 21, 2021

Related U.S. Application Data

(63) Continuation of application No. PCT/JP2019/042028, filed on Oct. 25, 2019.

(30) Foreign Application Priority Data

Dec. 28, 2018  (JP) ................................ 2018-248177

(51) Int. Cl.
*H01L 31/12* (2006.01)
*G01J 1/04* (2006.01)
(Continued)

(52) U.S. Cl.
CPC ............ *H01L 31/12* (2013.01); *G01J 1/0492* (2013.01); *G01J 1/4228* (2013.01); *G06T 1/0007* (2013.01);
(Continued)

(58) Field of Classification Search
CPC .. G06T 1/0007; G06V 10/143; G06V 10/147; G06V 40/1318; G06V 40/1341;
(Continued)

(56) References Cited

U.S. PATENT DOCUMENTS

| 5,875,269 A | 2/1999 | Yamashita et al. |
| 2002/0121590 A1 | 9/2002 | Yoshida et al. |

(Continued)

FOREIGN PATENT DOCUMENTS

| JP | H09-181883 A | 7/1997 |
| JP | 2003-169191 A | 6/2003 |

(Continued)

OTHER PUBLICATIONS

Japanese Office Action dated Jun. 21, 2022 in corresponding Japanese Application No. 2020-562857.

(Continued)

*Primary Examiner* — Jennifer D Bennett
(74) *Attorney, Agent, or Firm* — K&L Gates LLP

(57) ABSTRACT

A detection device is provided. The detection device includes a sensor base; a plurality of photoelectric conversion elements that are provided in a detection area of the sensor base and are configured to receive light incident thereon and output signals corresponding to the received light; a plurality of switching elements provided in the respective photoelectric conversion elements; a plurality of gate lines that are coupled to the switching elements and extend in a first direction; a first light source configured to emit first light having a first maximum emission wavelength;

(Continued)

and a second light source configured to emit second light having a second maximum emission wavelength.

5 Claims, 20 Drawing Sheets

(51) Int. Cl.

| | |
|---|---|
| *G01J 1/42* | (2006.01) |
| *H01L 27/146* | (2006.01) |
| *H01L 31/167* | (2006.01) |
| *G06V 40/13* | (2022.01) |
| *G06T 1/00* | (2006.01) |
| *G06V 40/14* | (2022.01) |
| *G06V 40/10* | (2022.01) |
| *G06V 40/70* | (2022.01) |
| *G06V 40/12* | (2022.01) |

(52) U.S. Cl.
CPC .... *G06V 40/1318* (2022.01); *H01L 27/14612* (2013.01); *H01L 27/14621* (2013.01); *H01L 27/14636* (2013.01); *H01L 31/167* (2013.01); *A61B 2562/0233* (2013.01); *G06V 40/1341* (2022.01); *G06V 40/14* (2022.01); *G06V 40/15* (2022.01); *G06V 40/70* (2022.01)

(58) Field of Classification Search
CPC ........ G06V 40/14; G06V 40/15; G06V 40/70; G01J 1/0492; G01J 1/4228; H01L 27/14612; H01L 27/14621; H01L 27/14636; H01L 31/167; H01L 31/12; A61B 2562/0233; A61B 5/1172
See application file for complete search history.

(56) References Cited

U.S. PATENT DOCUMENTS

| | | | | |
|---|---|---|---|---|
| 2003/0103686 | A1* | 6/2003 | Ogura | .................. G06V 40/145 |
| | | | | 382/321 |
| 2003/0147550 | A1 | 8/2003 | Shigeta | |
| 2004/0080614 | A1 | 4/2004 | Uemura | |
| 2004/0100668 | A1 | 5/2004 | Yoshida | |
| 2006/0204062 | A1* | 9/2006 | Shigeta | .................. G06V 40/13 |
| | | | | 382/124 |
| 2008/0075330 | A1* | 3/2008 | Matsumura | .............. G06K 9/00 |
| | | | | 382/115 |
| 2008/0117321 | A1 | 5/2008 | Muramatsu | |
| 2008/0157921 | A1* | 7/2008 | Hendriks | ............... G06V 40/13 |
| | | | | 340/5.83 |
| 2009/0027358 | A1 | 1/2009 | Hosono | |
| 2010/0245556 | A1 | 9/2010 | Kanda et al. | |
| 2013/0075761 | A1 | 3/2013 | Akiyama | |
| 2014/0350366 | A1 | 11/2014 | Akiyama | |
| 2015/0331508 | A1* | 11/2015 | Nho | ..................... H01L 27/323 |
| | | | | 345/173 |
| 2017/0264771 | A1 | 9/2017 | Inomoto et al. | |
| 2017/0337412 | A1 | 11/2017 | Bhat et al. | |
| 2018/0012069 | A1 | 1/2018 | Chung et al. | |
| 2019/0125221 | A1 | 5/2019 | Kobayashi et al. | |
| 2019/0378880 | A1 | 12/2019 | Zalar et al. | |
| 2020/0210668 | A1* | 7/2020 | Jhang | ................... G06F 3/0447 |

FOREIGN PATENT DOCUMENTS

| | | |
|---|---|---|
| JP | 2009-032005 A | 2/2009 |
| JP | 2010-231336 A | 10/2010 |
| JP | 2007179434 | 7/2012 |
| JP | 2013-073965 A | 4/2013 |
| JP | 2015-176457 | 10/2015 |
| JP | 2017-163477 A | 9/2017 |
| JP | 2017-196319 | 11/2017 |
| JP | 2007243265 | 9/2020 |
| JP | 2003233806 | 8/2022 |
| WO | 2015/119078 | 3/2017 |
| WO | 2018/131638 A1 | 7/2018 |

OTHER PUBLICATIONS

Tomoyuki Yokota, Peter Zalar, Martin Kaltenbrunner, Hiroaki Jinno, Naoji Matsuhisa, Hiroki Kitanosako, Yutaro Tachibana, Wakako Yukita, Mari Koizumi, Takao Someya, "Ultraflexible organic photonic skin," Science Advances Apr. 15, 2016: vol. 2, No. 4, e1501856 DOI: 10.1126/sciadv.1501856.
International Search Report dated Dec. 17, 2019 in connection with PCT/JP2019/042028.
Japanese Office Action dated Mar. 29, 2022 in corresponding Japanese Application No. 2020-562857.
Japanese Office Action dated Jul. 4, 2023 in corresponding Japanese Application No. 2022-141831.

* cited by examiner

DETECTION DEVICE INCLUDING LIGHT SOURCES ALONG AN OUTER CIRCUMFERENCE OF TWO DETECTION AREAS EACH OF THE DETECTION AREAS HAVING A SPECIFIC SCAN DIRECTION

CROSS-REFERENCE TO RELATED APPLICATION

This application claims the benefit of priority from Japanese Patent Application No. 2018-248177 filed on Dec. 28, 2018 and International Patent Application No. PCT/JP2019/042028 filed on Oct. 25, 2019, the entire contents of which are incorporated herein by reference.

BACKGROUND

1. Technical Field

What is disclosed herein relates to a detection device.

2. Description of the Related Art

United States Patent Application Publication No. 2018/0012069 (US-A-2018/0012069) describes an optical sensor in which a plurality of photoelectric conversion elements such as photodiodes are arranged on a semiconductor substrate. In the optical sensor, signals output from the photoelectric conversion elements change with an amount of irradiating light, and thus, biological information can be detected. The optical sensor of US-A-2018/0012069 can detect asperities of a surface of a finger at a fine pitch and is used as a fingerprint sensor. Japanese Patent Application Laid-open Publication No. 2009-32005 (JP-A-2009-32005) describes a display device provided with a plurality of sensors for detecting infrared rays. The display device of JP-A-2009-32005 can detect a position of a finger, a fingerprint pattern, and a vein pattern based on reflected light of the infrared rays.

The optical sensor is required to detect not only a shape of a fingerprint of a detection target object such as a finger or a palm, but also various types of the biological information on the detection target object. The techniques of US-A-2018/0012069 and JP-A-2009-32005 may be difficult to detect a plurality of different types of the biological information using the same sensor.

SUMMARY

A detection device according to an aspect of the present disclosure includes: a sensor base; a plurality of photoelectric conversion elements that are provided in a detection area of the sensor base and are configured to receive light incident thereon and output signals corresponding to the received light; a plurality of switching elements provided in the respective photoelectric conversion elements; a plurality of gate lines that are coupled to the switching elements and extend in a first direction; a first light source configured to emit first light having a first maximum emission wavelength; and a second light source configured to emit second light having a second maximum emission wavelength.

DETAILED DESCRIPTION

Figure 1:
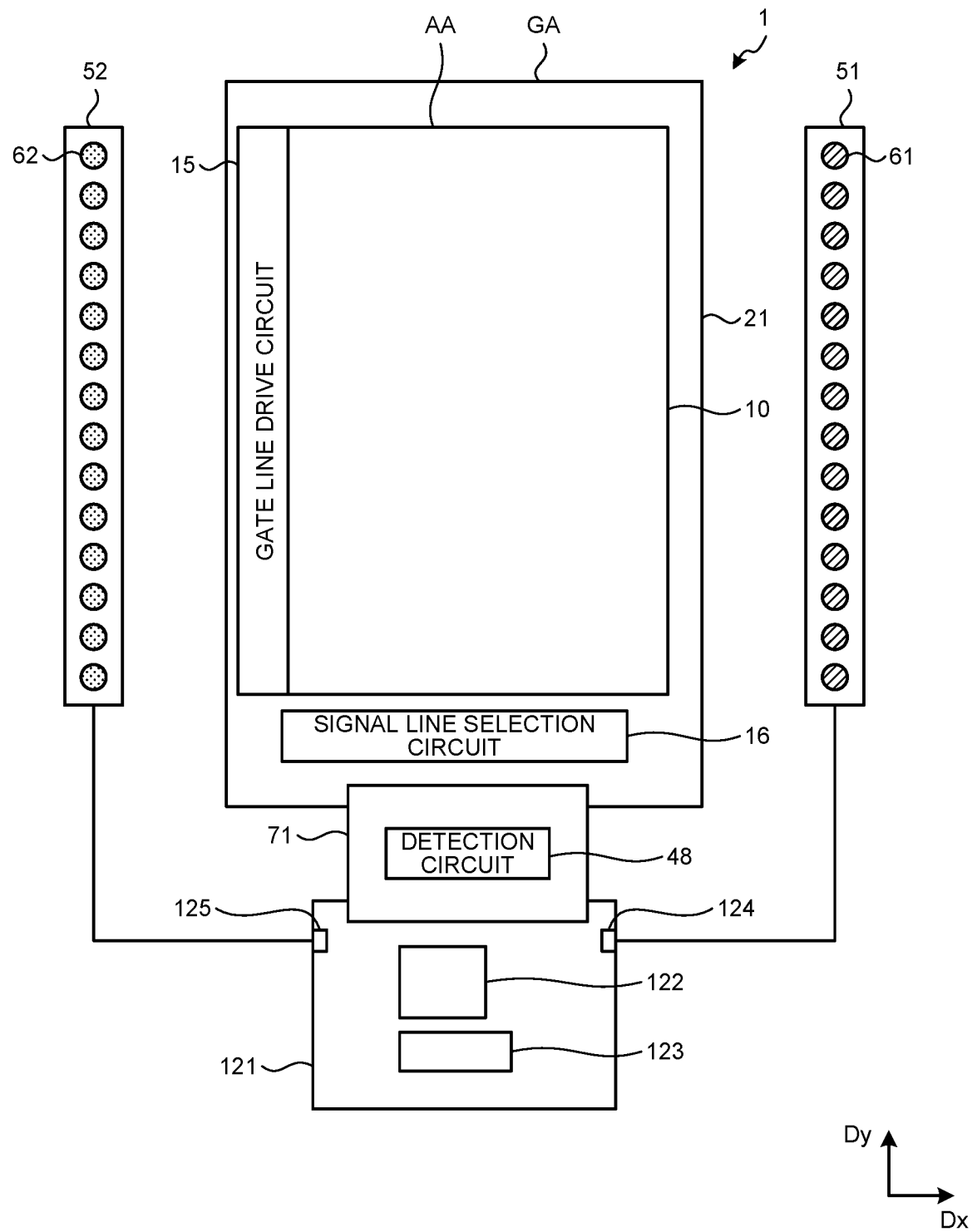
FIG. 1 is a plan view illustrating a detection device according to a first embodiment.

The following describes embodiments for carrying out the present disclosure in detail with reference to the drawings. The present disclosure is not limited to the description of the embodiments given below. Components described below include those easily conceivable by those skilled in the art or those substantially identical thereto. Moreover, the components described below can be appropriately combined. The disclosure is merely an example, and the present disclosure naturally encompasses appropriate modifications easily conceivable by those skilled in the art while maintaining the gist of the disclosure. To further clarify the description, the drawings schematically illustrate, for example, widths, thicknesses, and shapes of various parts as compared with actual aspects thereof, in some cases. However, they are merely examples, and interpretation of the present disclosure is not limited thereto. The same element as that illustrated in a drawing that has already been discussed is denoted by the same reference numeral through the description and the drawings, and detailed description thereof will not be repeated in some cases where appropriate.

In this disclosure, when an element is described as being "on" another element, the element can be directly on the other element, or there can be one or more elements between the element and the other element.

First Embodiment

FIG. 1 is a plan view illustrating a detection device according to a first embodiment. As illustrated in FIG. 1, a detection device 1 includes a sensor base 21, a sensor 10, a gate line drive circuit 15, a signal line selection circuit 16, a detection circuit 48, a control circuit 122, a power supply circuit 123, a first light source base 51, a second light source base 52, first light sources 61, and second light sources 62.

A control board 121 is electrically coupled to the sensor base 21 through a flexible printed circuit board 71. The flexible printed circuit board 71 is provided with the detection circuit 48. The control board 121 is provided with the control circuit 122 and the power supply circuit 123. The control circuit 122 is, for example, a field programmable gate array (FPGA). The control circuit 122 supplies control signals to the sensor 10, the gate line drive circuit 15, and the signal line selection circuit 16 to control a detection operation of the sensor 10. The control circuit 122 supplies control signals to the first light sources 61 and the second light sources 62 to control the turning on or off of the first light sources 61 and the second light sources 62. The power supply circuit 123 supplies voltage signals including, for example, a sensor power supply signal VDDSNS (refer to FIG. 4) to the sensor 10, the gate line drive circuit 15, and the signal line selection circuit 16. The power supply circuit 123 also supplies a power supply voltage to the first light sources 61 and the second light sources 62.

The sensor base 21 has a detection area AA and a peripheral area GA. The detection area AA is an area provided with a plurality of photodiodes PD (refer to FIG. 4) included in the sensor 10. The peripheral area GA is an area between the outer circumference of the detection area AA and ends of the sensor base 21 and is an area not overlapping the photodiodes PD.

The gate line drive circuit 15 and the signal line selection circuit 16 are provided in the peripheral area GA. Specifically, the gate line drive circuit 15 is provided in an area of the peripheral area GA extending along a second direction Dy, and the signal line selection circuit 16 is provided in an area of the peripheral area GA extending along a first direction Dx and is provided between the sensor 10 and the detection circuit 48.

The first direction Dx is a direction in a plane parallel to the sensor base 21. The second direction Dy is a direction in a plane parallel to the sensor base 21 and is a direction orthogonal to the first direction Dx. The second direction Dy may intersect the first direction Dx without being orthogonal thereto. A third direction Dz is a direction orthogonal to the first direction Dx and the second direction Dy and is the normal direction of the sensor base 21.

The first light sources 61 are provided on the first light source base 51 and are arranged along the second direction Dy. The second light sources 62 are provided on the second light source base 52, and are arranged along the second direction Dy. The first light source base 51 and the second light source base 52 are electrically coupled through terminals 124 and 125, respectively, provided on the control board 121 to the control circuit 122 and the power supply circuit 123.

For example, inorganic light-emitting diodes (LEDs) or organic electroluminescent (EL) diodes (organic light-emitting diodes (OLEDs)) are used as the first light sources 61 and the second light sources 62. The first light sources 61 and the second light sources 62 emit first light L61 and second light L62 (refer to FIG. 9), respectively, having different wavelengths. That is, the first light L61 has a first maximum emission wavelength MW1, and the second light L62 has a second maximum emission wavelength different from the first maximum emission wavelength MW1. The term "maximum emission wavelength" refers to a wavelength that exhibits the maximum emission intensity in an emission spectrum representing a relation between the wavelength and the emission intensity of each of the first light L61 and the second light L62.

Figure 26:
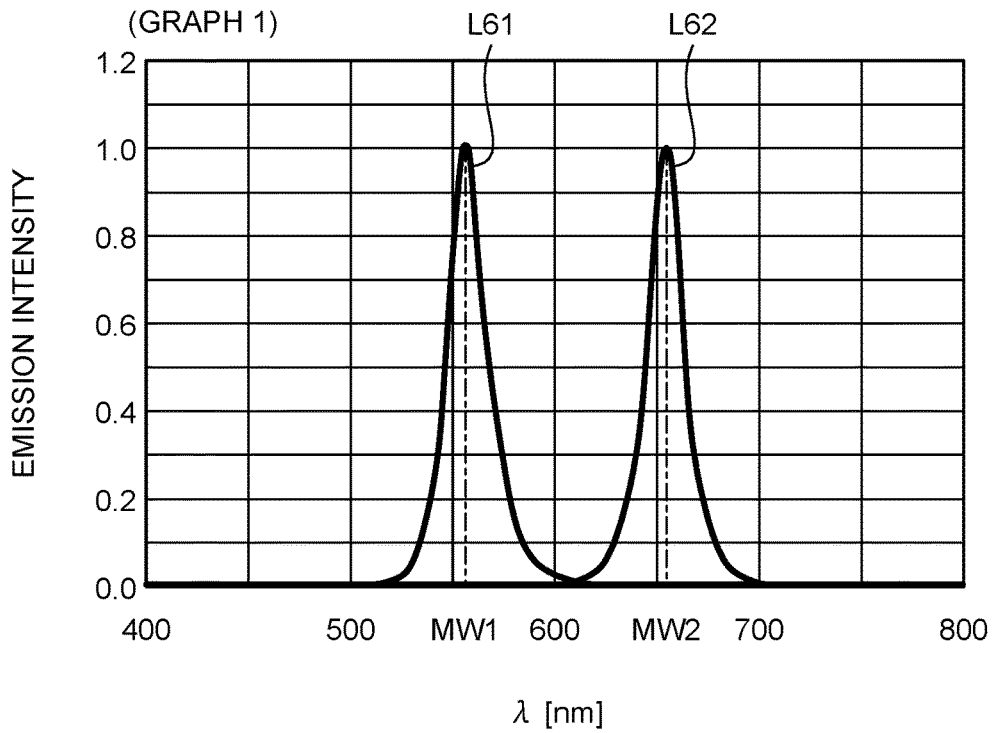
FIG. 26 is a graph illustrating an example of an emission spectrum of first light and second light.

FIG. 26 is a graph illustrating an example of the emission spectrum of the first light and the second light. In Graph 1 illustrated in FIG. 26, the horizontal axis represents the wavelength, and the vertical axis represents the emission intensity. As an example, as illustrated in FIG. 26, the first light L61 has the first maximum emission wavelength MW1 in a range from 520 nm to 600 nm, for example, at approximately 560 nm, and the second light L62 has a second maximum emission wavelength MW2 in a range from 600 nm to 700 nm, for example, at approximately 660 nm. That is, the second maximum emission wavelength MW2 of the second light L62 is longer than the first maximum emission wavelength MW1 of the first light L61. In this case, the first light L61 and the second light L62 are visible light. The first light L61 is blue or green light, and the second light L62 is red light.

The first light L61 emitted from the first light sources 61 is reflected on a surface of a detection target object, for example, a finger Fg, and enters the sensor 10. Thus, the sensor can detect a fingerprint by detecting a shape of asperities of the surface of, for example, the finger Fg. The second light L62 emitted from the second light sources 62 is reflected inside, for example, the finger Fg, or transmitted through, for example, the finger Fg, and enters the sensor 10. Thus, the sensor 10 can detect biological information inside, for example, the finger Fg. The biological information is, for example, pulsation of the finger Fg or a palm.

Figure 27:
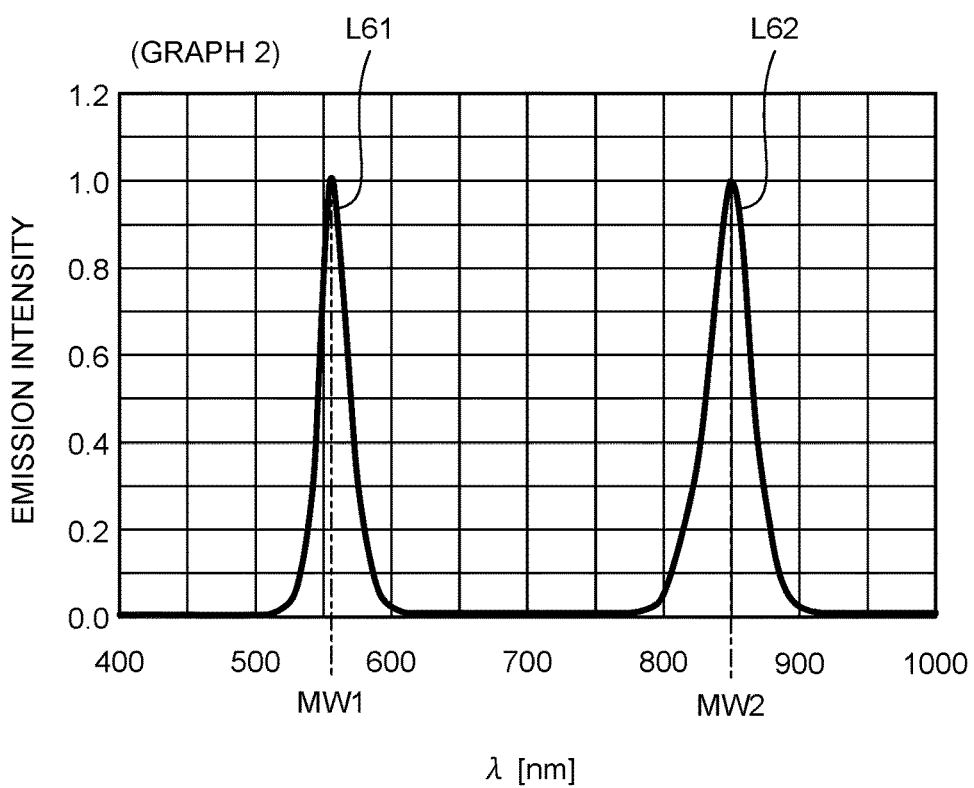
FIG. 27 is a graph illustrating another example of the emission spectrum of the first light and the second light.

The wavelength of each of the first light L61 and the second light L62 is not limited to the example described above, and can be changed as appropriate. FIG. 27 is a graph illustrating another example of the emission spectrum of the first light and the second light. For example, as illustrated in Graph 2 of FIG. 27, the first light L61 may have the first maximum emission wavelength MW1 in the range from 520 nm to 600 nm, for example, at approximately 560 nm, and the second light L62 may have the second maximum emission wavelength MW2 in a range from 780 nm to 900 nm, for example, at approximately 850 nm. In this case, the first light L61 is blue or green visible light, and the second light L62 is infrared light. The sensor 10 can detect the fingerprint based on the first light L61 emitted from the first light sources 61. The second light L62 emitted from the second light sources 62 is reflected inside the detection target object such as the finger Fg, or transmitted through, for example, the finger Fg, and enters the sensor 10. Thus, the sensor 10 can detect a blood vessel image (vein pattern) as the biological information inside, for example, the finger Fg.

Alternatively, the first light L61 may have the first maximum emission wavelength MW1 in the range from 600 nm to 700 nm, for example, at approximately 660 nm, and the second light L62 may have the second maximum emission wavelength MW2 in the range from 780 nm to 900 nm, for example, at approximately 850 nm. In this case, the sensor 10 can detect a blood oxygen concentration in addition to the pulsation and the blood vessel image as the biological information based on the first light L61 emitted from the first light sources 61 and the second light L62 emitted from the second light sources 62. In this manner, since the detection device 1 includes the first light sources 61 and the second light sources 62, the detection device 1 can detect the various types of the biological information by performing the detection based on the first light L61 and the detection based on the second light L62.

The arrangement of the first light sources 61 and the second light sources 62 illustrated in FIG. 1 is merely an example, and can be changed as appropriate. For example, the first light sources 61 and the second light sources 62 may be arranged on each of the first light source base 51 and the second light source base 52. In this case, a group including the first light sources 61 and a group including the second light sources 62 may be arranged in the second direction Dy, or the first light source 61 and the second light source 62 may be alternately arranged in the second direction Dy. The number of the light source bases provided with the first light sources 61 and the second light sources 62 may be one, or three or more.

Figure 2:
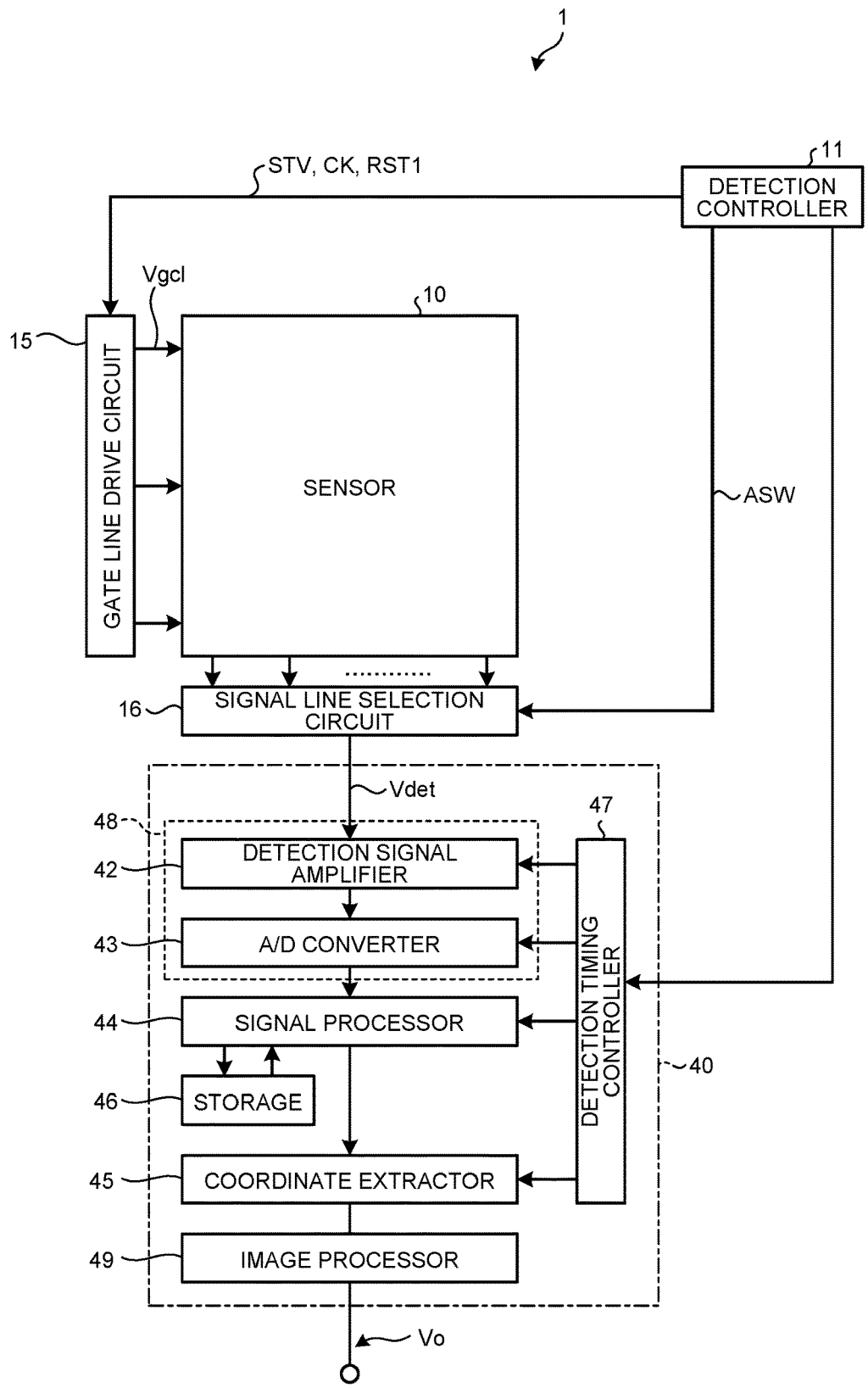
FIG. 2 is a block diagram illustrating a configuration example of the detection device according to the first embodiment.

FIG. 2 is a block diagram illustrating a configuration example of the detection device according to the first embodiment. As illustrated in FIG. 2, the detection device 1 further includes a detection controller 11 and a detector 40. The control circuit 122 includes some or all functions of the detection controller 11. The control circuit 122 also includes some or all functions of the detector 40 except those of the detection circuit 48.

The sensor 10 is an optical sensor including the photodiodes PD serving as photoelectric conversion elements. Each of the photodiodes PD included in the sensor 10 outputs an electrical signal corresponding to light emitted thereto as a detection signal Vdet to the signal line selection circuit 16. The sensor 10 performs the detection in response to a gate drive signal Vgcl supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including, for example, a start signal STV, a clock signal CK, and a reset signal RST1 to the gate line drive circuit 15. The detection controller 11 also supplies various control signals including, for example, a selection signal ASW to the signal line selection circuit 16. The detection controller 11 also supplies various control signals to the first light sources 61 and the second light sources 62 to control the turning on and off of the first light sources 61 and the second light sources 62.

The gate line drive circuit 15 is a circuit that drives a plurality of gate lines GCL (refer to FIG. 3) based on the various control signals. The gate line drive circuit 15 sequentially or simultaneously selects the gate lines GCL and supplies the gate drive signals Vgcl to the selected gate lines GCL. Through this operation, the gate line drive circuit 15 selects the photodiodes PD coupled to the gate lines GCL.

Figure 3:
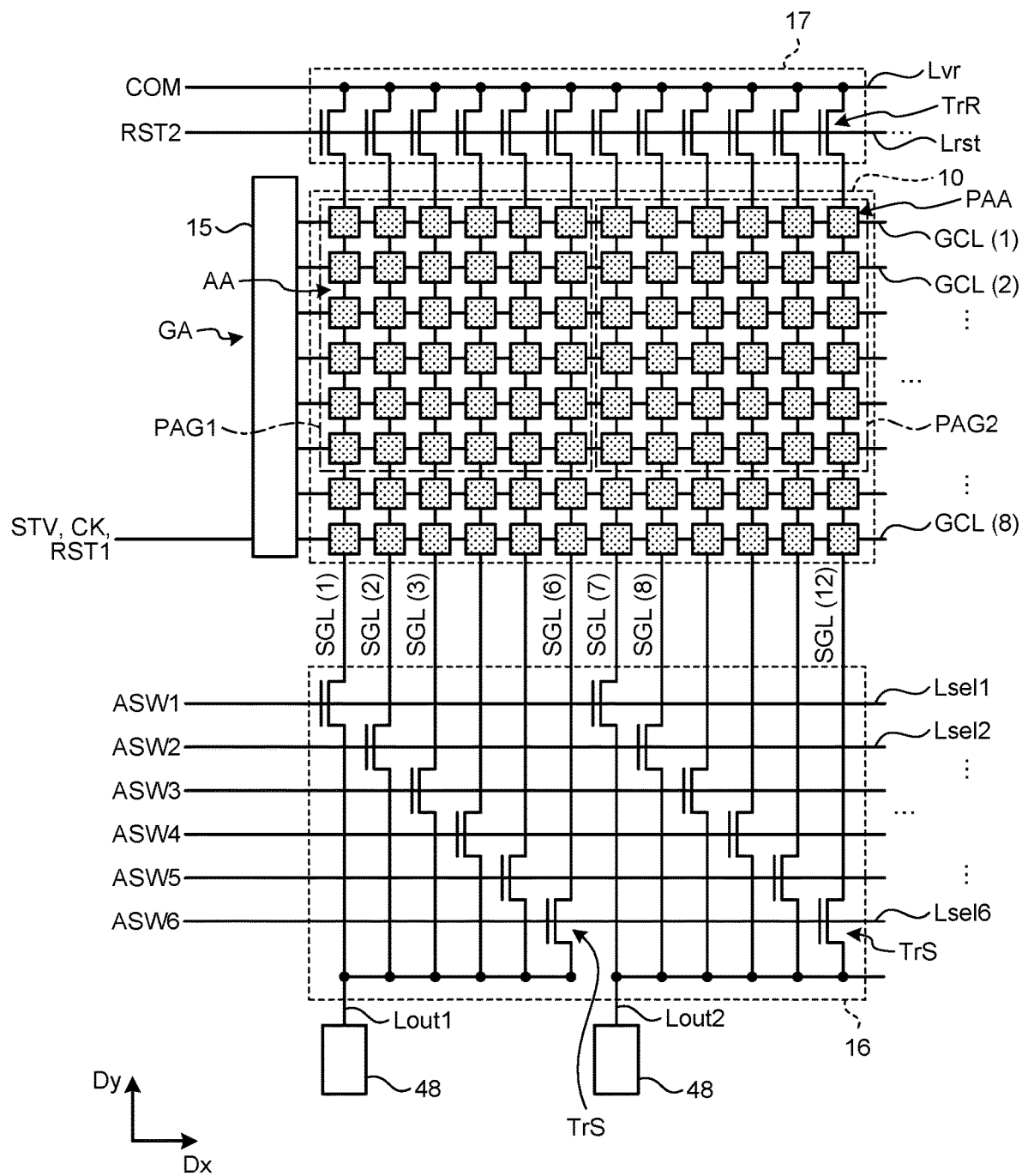
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 is, for example, a multiplexer. The signal line selection circuit 16 couples the selected signal lines SGL to the detection circuit 48 based on the selection signal ASW supplied from the detection controller 11. Through this operation, the signal line selection circuit 16 outputs the detection signal Vdet of each of the photodiodes PD to the detector 40.

The detector 40 includes the detection circuit 48, a signal processor 44, a coordinate extractor 45, a storage 46, a detection timing controller 47, and an image processor 49. Based on a control signal supplied from the detection controller 11, the detection timing controller 47 controls the detection circuit 48, the signal processor 44, the coordinate extractor 45, and the image processor 49 so as to operate in synchronization with one another.

The detection circuit 48 is, for example, an analog front end (AFE) circuit. The detection circuit 48 is a signal processing circuit having functions of at least a detection signal amplifier 42 and an analog-to digital (A/D) converter 43. The detection signal amplifier 42 amplifies the detection signal Vdet. The A/D converter 43 converts an analog signal output from the detection signal amplifier 42 into a digital signal.

The signal processor 44 is a logic circuit that detects a predetermined physical quantity received by the sensor 10 based on an output signal of the detection circuit 48. When the finger Fg is in contact with or in proximity to a detection surface, the signal processor 44 can detect the asperities on the surface of the finger Fg or the palm based on the signal from the detection circuit 48. The signal processor 44 can also detect the biological information based on the signal from the detection circuit 48. The biological information is, for example, the blood vessel image, a pulse wave, the pulsation, and/or the blood oxygen concentration of the finger Fg or the palm.

The signal processor 44 may acquire the detection signals Vdet (biological information) simultaneously detected by the photodiodes PD and average the detection signals Vdet. In this case, the detector 40 can perform the stable detection by reducing a measurement error caused by noise or a relative displacement between the detection target object such as the finger Fg and the sensor 10.

The storage 46 temporarily stores a signal calculated by the signal processor 44. The storage 46 may be, for example, a random access memory (RAM) or a register circuit.

The coordinate extractor 45 is a logic circuit that obtains, when the contact or the proximity of the finger is detected by the signal processor 44, detection coordinates of the asperities on the surface of, for example, the finger. The coordinate extractor 45 is also a logic circuit that obtains detected coordinates of blood vessels of the finger Fg or the palm. The image processor 49 combines the detection signals Vdet output from the respective photodiodes PD of the sensor 10 to generate two-dimensional information representing the shape of the asperities on the surface of, for example, the finger Fg and two-dimensional information representing a shape of the blood vessels of the finger Fg or the palm. The coordinate extractor 45 may output the detection signals Vdet as sensor outputs Vo, without calculating the detection coordinates. There may be a case where the coordinate extractor 45 and the image processor 49 are not included in the detector 40.

Figure 4:
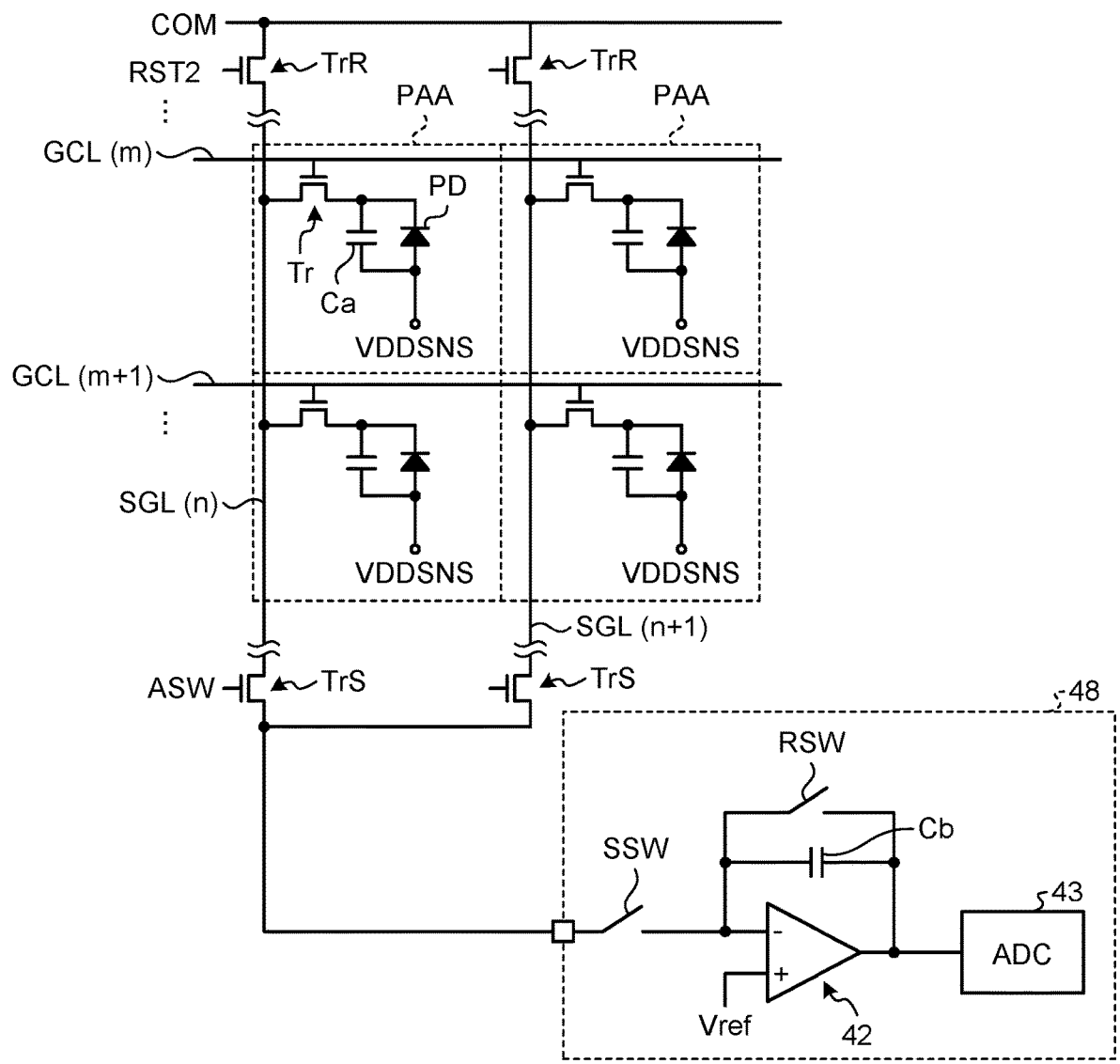
FIG. 4 is a circuit diagram illustrating a plurality of partial detection areas.

The following describes a circuit configuration example of the detection device 1. FIG. 3 is a circuit diagram illustrating the detection device. FIG. 4 is a circuit diagram illustrating a plurality of partial detection areas. FIG. 4 also illustrates a circuit configuration of the detection circuit 48.

As illustrated in FIG. 3, the sensor 10 has a plurality of partial detection areas PAA arranged in a matrix having a row-column configuration. Each of the partial detection areas PAA is provided with the photodiode PD.

The gate lines GCL extend in the first direction Dx, and are coupled to the partial detection areas PAA arranged in the first direction Dx. A plurality of gate lines GCL(1), GCL(2), . . . , GCL(8) are arranged in the second direction Dy, and are each coupled to the gate line drive circuit 15. In the following description, the gate lines GCL(1), GCL(2), . . . , GCL(8) will each be simply referred to as the gate line GCL when they need not be distinguished from one another. For ease of understanding of the description, FIG. 3 illustrates eight gate lines GCL. However, this is merely an example, and M gate lines GCL (where M is eight or larger, and is, for example, 256) may be arranged.

The signal lines SGL extend in the second direction Dy and are coupled to the photodiodes PD of the partial detection areas PAA arranged in the second direction Dy. A plurality of signal lines SGL(1), SGL(2), . . . , SGL(12) are arranged in the first direction Dx and are each coupled to the signal line selection circuit 16 and a reset circuit 17. In the following description, the signal lines SGL(1), SGL(2), . . . , SGL(12) will each be simply referred to as the signal line SGL when need not be distinguished from one another.

For ease of understanding of the description, 12 signal lines SGL are illustrated. However, this is merely an example, and N signal lines SGL (where N is 12 or larger, and is, for example, 252) may be arranged. In FIG. 3, the sensor 10 is provided between the signal line selection circuit 16 and the reset circuit 17. The configuration is not limited thereto. The signal line selection circuit 16 and the reset circuit 17 may be coupled to ends in the same direction of the signal lines SGL. One sensor has an area of substantially 50×50 µm², for example. The detection area AA has a resolution of substantially 508 pixels per inch (ppi), for example. The number of sensors arranged in the detection area AA is, for example, 252 cells×256 cells. The detection area AA has an area of, for example, 12.6×12.8 mm².

The gate line drive circuit 15 receives the various control signals such as the start signal STV, the clock signal CK, and the reset signal RST1 from the control circuit 122 (refer to FIG. 2). The gate line drive circuit 15 sequentially selects the gate lines GCL(1), GCL(2), . . . , GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the partial detection areas PAA arranged in the first direction Dx are selected as detection targets.

The gate line drive circuit 15 may perform different driving for each of detection modes including the detection of the fingerprint and the detection of different items of the biological information (such as the pulse wave, the pulsation, the blood vessel image, and the blood oxygen concentration). For example, the gate line drive circuit 15 may drive more than one gate line GCL in a bundle.

Specifically, the gate line drive circuit 15 simultaneously selects a predetermined number of the gate lines GCL from among the gate lines GCL(1), GCL(2), GCL(8) based on the control signals. For example, the gate line drive circuit 15 simultaneously selects six gate lines GCL(1) to GCL(6) and supplies thereto the gate drive signals Vgcl. The gate line drive circuit 15 supplies the gate drive signals Vgcl through the selected six gate lines GCL to the first switching elements Tr. Through this operation, detection area groups PAG1 and PAG2 each including more than one partial detection area PAA arranged in the first direction Dx and the second direction Dy are selected as the respective detection targets. The gate line drive circuit 15 drives the predetermined number of the gate lines GCL in a bundle, and sequentially supplies the gate drive signals Vgcl to each of the predetermined number of the gate lines GCL.

The signal line selection circuit 16 includes a plurality of selection signal lines Lsel, a plurality of output signal lines Lout, and third switching elements TrS. The third switching elements TrS are provided corresponding to the signal lines SGL. Six signal lines SGL(1), SGL(2), . . . , SGL(6) are coupled to a common output signal line Lout1. Six signal lines SGL(7), SGL(8), . . . , SGL(12) are coupled to a common output signal line Lout2. The output signal lines Lout1 and Lout2 are each coupled to the detection circuit 48.

The signal lines SGL(1), SGL(2), . . . , SGL(6) are grouped into a first signal line block, and the signal lines SGL(7), SGL(8), . . . , SGL(12) are grouped into a second signal line block. The selection signal lines Lsel are coupled to the gates of the third switching elements TrS included in one of the signal line blocks, respectively. One of the selection signal lines Lsel is coupled to the gates of the third switching elements TrS in the signal line blocks.

Specifically, selection signal lines Lsel1, Lsel2, . . . , Lsel6 are coupled to the third switching elements TrS corresponding to the signal lines SGL(1), SGL(2), . . . , SGL(6), respectively. The selection signal line Lsel1 is coupled to the third switching element TrS corresponding to the signal line SGL(1) and the third switching element TrS corresponding to the signal line SGL(7). The selection signal line Lsel2 is coupled to the third switching element TrS corresponding to the signal line SGL(2) and the third switching element TrS corresponding to the signal line SGL(8).

The control circuit 122 (refer to FIG. 1) sequentially supplies the selection signal ASW to the selection signal lines Lsel. Through the operations of the third switching elements TrS, the signal line selection circuit 16 sequentially selects the signal lines SGL in one of the signal line blocks in a time-division manner. The signal line selection circuit 16 selects one of the signal lines SGL respectively in each of the signal line blocks. With the above-described configuration, the detection device 1 can reduce the number of integrated circuits (ICs) including the detection circuit 48 or the number of terminals of the ICs.

The signal line selection circuit 16 may couple more than one signal line SGL to the detection circuit 48 in a bundle. Specifically, the control circuit 122 (refer to FIG. 1) simultaneously supplies the selection signal ASW to the selection signal lines Lsel. With this operation, the signal line selection circuit 16 selects, by the operations of the third switching elements TrS, the signal lines SGL (for example, six of the signal lines SGL) in one of the signal line blocks, and couple the signal lines SGL to the detection circuit 48. As a result, signals detected in the detection area groups PAG1 and PAG2 are output to the detection circuit 48. In this case, signals from the partial detection areas PAA (photodiodes PD) included in the detection area groups PAG1 and PAG2 are put together and output to the detection circuit 48.

By the operations of the gate line drive circuit 15 and the signal line selection circuit 16, the detection is performed for each of the detection area groups PAG1 and PAG2. As a result, the intensity of the detection signal Vdet obtained by one time of detection increases, so that the sensor sensitivity can be improved. In addition, time required for the detection can be reduced. Consequently, the detection device 1 can repeat to perform the detection in a short time, and thus, can improve a signal-to-noise (S/N) ratio, and can accurately detect a change in the biological information with time such as the pulse wave.

As illustrated in FIG. 3, the reset circuit 17 includes a reference signal line Lvr, a reset signal line Lrst, and fourth switching elements TrR. The fourth switching elements TrR are provided corresponding to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 4) included in each of the partial detection areas PAA.

As illustrated in FIG. 4, each of the partial detection area PAA includes the photodiode PD, the capacitive element Ca, and the first switching element Tr. FIG. 4 illustrates two gate lines GCL(m) and GCL(m+1) arranged in the second direction Dy among the gate lines GCL and illustrates two signal lines SGL(n) and SGL(n+1) arranged in the first direction Dx among the signal lines SGL. The partial detection area PAA is an area surrounded by the gate lines GCL and the signal lines SGL. Each of the first switching elements Tr is provided corresponding to each of the photodiodes PD. The first switching element Tr includes a thin-film transistor, and in this example, includes an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the photodiode PD and the capacitive element Ca.

The anode of the photodiode PD is supplied with the sensor power supply signal VDDSNS from the power supply circuit 123. The signal line SGL and the capacitive element Ca are supplied with the reference signal COM that serves as an initial potential of the signal line SGL and the capacitive element Ca from the power supply circuit 123.

When the partial detection area PAA is irradiated with light, a current corresponding to an amount of the light flows through the photodiode PD. As a result, an electrical charge is stored in the capacitive element Ca. After the first switching element Tr is turned on, a current corresponding to the electrical charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the amount of the light irradiating the photodiode PD in each of the partial detection areas PAA or signals corresponding to the amounts of the light irradiating the photodiodes PD in each of the detection area groups PAG1 and PAG2.

During a reading period Pdet (refer to FIG. 7), a switch SSW of the detection circuit 48 is turned on, and the detection circuit 48 is coupled to the signal lines SGL. The detection signal amplifier 42 of the detection circuit 48 converts a variation of a current supplied from the signal lines SGL into a variation of a voltage, and amplifies the result. A reference voltage Vref having a fixed potential is supplied to a non-inverting input portion (+) of the detection signal amplifier 42, and the signal lines SGL are coupled to an inverting input portion (−) of the detection signal amplifier 42. In the present embodiment, the same signal as the reference signal COM is supplied as the reference voltage Vref. The detection signal amplifier 42 includes a capacitive element Cb and a reset switch RSW. During a reset period Prst (refer to FIG. 7), the reset switch RSW is turned on, and an electrical charge of the capacitive element Cb is reset.

Figure 5:
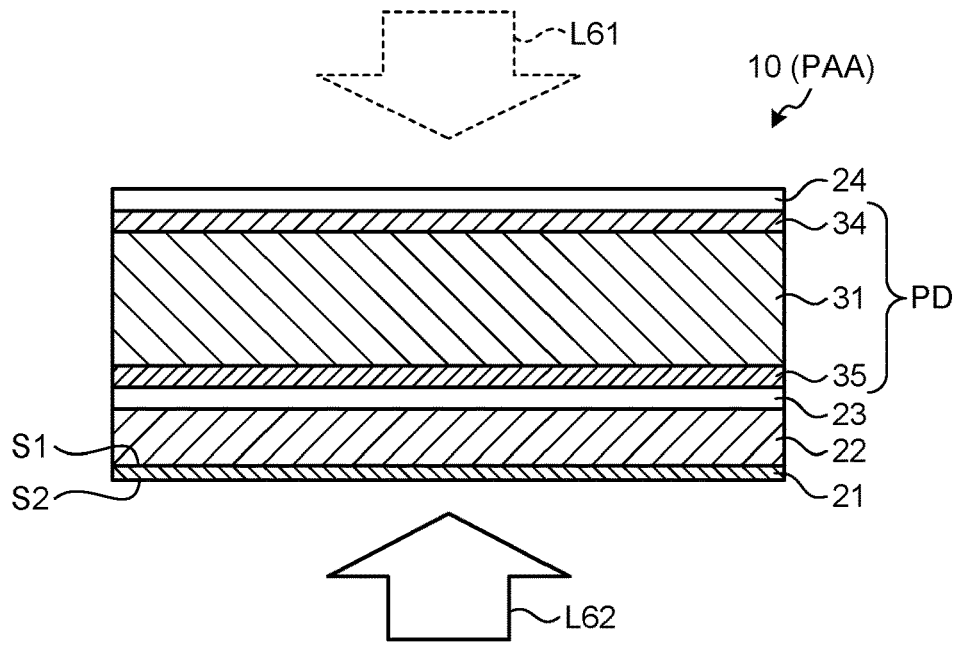
FIG. 5 is a sectional view illustrating a schematic sectional configuration of a sensor.

The following describes a configuration of the photodiode PD. FIG. 5 is a sectional view illustrating a schematic sectional configuration of the sensor.

As illustrated in FIG. 5, the sensor 10 includes the sensor base 21, a TFT layer 22, an insulating layer 23, the photodiode PD, and a protection film 24. The sensor base 21 is an insulating base and is made using, for example, glass or resin material. The sensor base 21 is not limited to having a flat plate shape and may have a curved surface. In this case, the sensor base 21 may be made up of a film-shaped resin. The sensor base 21 has a first surface S1 and a second surface S2 on the opposite side of the first surface S1. The TFT layer 22, the insulating layer 23, the photodiode PD, and the protection film 24 are stacked on the first surface S1 in the order as listed.

The TFT layer 22 is provided with circuits such as the gate line drive circuit 15 and the signal line selection circuit 16 described above. The TFT layer 22 is also provided with thin-film transistors (TFTs), such as the first switching element Tr, and various types of wiring, such as the gate lines GCL and the signal lines SGL. The sensor base 21 and the TFT layer 22, which serve as a drive circuit board that drives the sensor for each predetermined detection area, are also called a backplane.

The insulating layer 23 is an inorganic insulating layer. For example, an oxide such as silicon oxide ($SiO_2$) or a nitride such as silicon nitride (SiN) is used as the insulating layer 23.

The photodiode PD is provided on the insulating layer 23. The photodiode PD includes a photoelectric conversion layer 31, a cathode electrode 35, and an anode electrode 34. The cathode electrode 35, the photoelectric conversion layer 31, and the anode electrode 34 are stacked in the order as listed, in a direction orthogonal to the first surface S1 of the sensor base 21. The stacking order in the photodiode PD may be as follows: the anode electrode 34, the photoelectric conversion layer 31, and the cathode electrode 35.

Characteristics (such as a voltage-current characteristic and a resistance value) of the photoelectric conversion layer 31 vary depending on the irradiating light. An organic material is used as the material of the photoelectric conversion layer 31. Specifically, a low-molecular organic material such as $C_{60}$ (fullerene), phenyl-$C_{61}$-butyric acid methyl ester (PCBM), copper phthalocyanine (CuPc), fluorinated copper phthalocyanine ($F_{16}$CuPc), rubrene (5,6,11,12-tetraphenyltetracene), or PDI (derivative of perylene) can be used as the photoelectric conversion layer 31.

The photoelectric conversion layer 31 can be formed by a vapor deposition method (dry process) using any of the above-listed low-molecular organic materials. In this case, the photoelectric conversion layer 31 may be a laminated film of CuPc and F16CuPc, or a laminated film of rubrene and $C_{60}$. The photoelectric conversion layer 31 can also be formed by an application method (wet process). In this case, a material obtained by combining any of the above-listed low-molecular organic materials with a polymeric organic material is used as the photoelectric conversion layer 31. For example, poly(3-hexylthiophene) (P3HT) or F8-alt-benzothiadiazole (F8BT) can be used as the polymeric organic material. The photoelectric conversion layer 31 can be a film formed by a mixture of P3HT and PCBM, or a film formed by a mixture of F8BT and PDI.

The cathode electrode 35 faces the anode electrode 34 with the photoelectric conversion layer 31 interposed therebetween. A light-transmitting conductive material such as indium tin oxide (ITO) is used as the anode electrode 34. A metal material such as silver (Ag) or aluminum (Al) is used as the cathode electrode 35. Alternatively, the cathode electrode 35 may be an alloy material containing at least one or more of these metal materials.

The cathode electrode 35 can be formed as a light-transmitting transflective electrode by controlling the film thickness of the cathode electrode 35. For example, the cathode electrode 35 is formed of an Ag thin film having a film thickness of 10 nm so as to have light transmittance of approximately 60%. In this case, the photodiode PD can detect light emitted from both surface sides of the sensor base 21, that is, for example, both the first light L61 emitted from the first surface S1 side and the second light L62 emitted from the second surface S2 side.

The protection film 24 is provided so as to cover the anode electrode 34. The protection film 24 is a passivation film and is provided to protect the photodiode PD.

Figure 6:
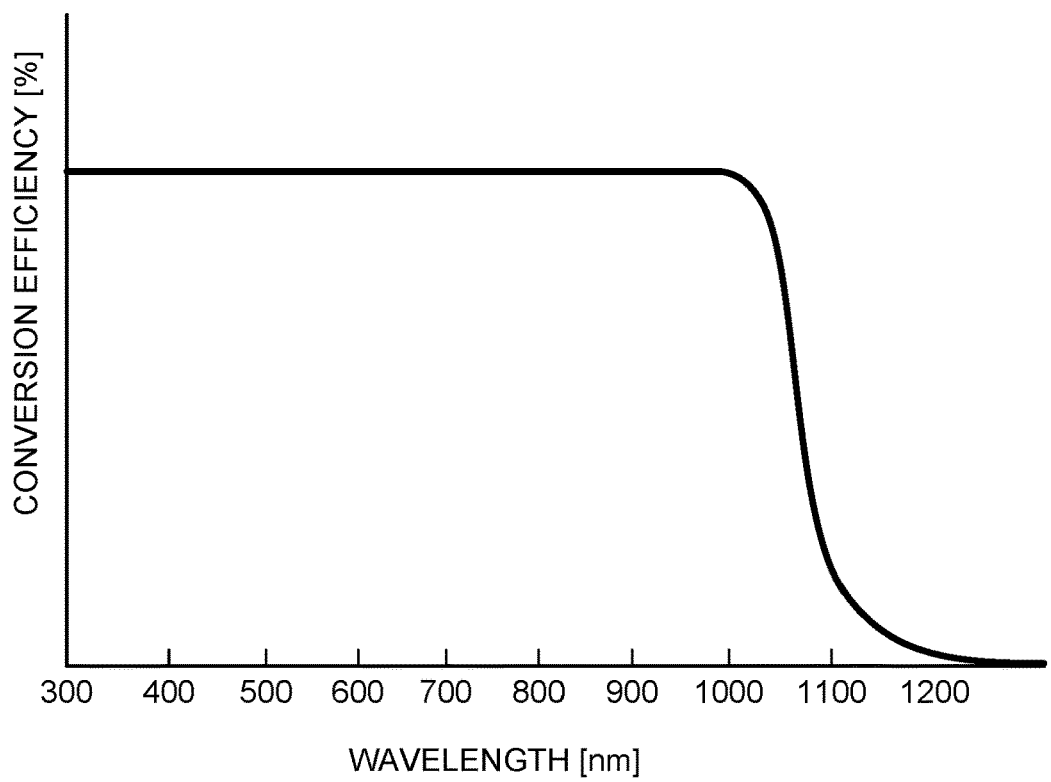
FIG. 6 is a graph schematically illustrating a relation between a wavelength and a conversion efficiency of light incident on a photodiode.

FIG. 6 is a graph schematically illustrating a relation between the wavelength and a conversion efficiency of light incident on the photodiode. The horizontal axis of the graph illustrated in FIG. 6 represents the wavelength of the light incident on the photodiode PD, and the vertical axis of the graph represents an external quantum efficiency of the photodiode PD. The external quantum efficiency is expressed as a ratio between the number of photons of the light incident on the photodiode PD and a current that flows from the photodiode PD to the external detection circuit 48.

As illustrated in FIG. 6, the photodiode PD has an excellent efficiency in a wavelength range from approximately 300 nm to approximately 1000 nm. That is, the photodiode PD has a sensitivity for wavelengths of both the first light L61 emitted from the first light sources 61 and the second light L62 emitted from the second light sources 62. Therefore, each of the photodiodes PD can detect a plurality of beams of light having different wavelengths.

Figure 7:
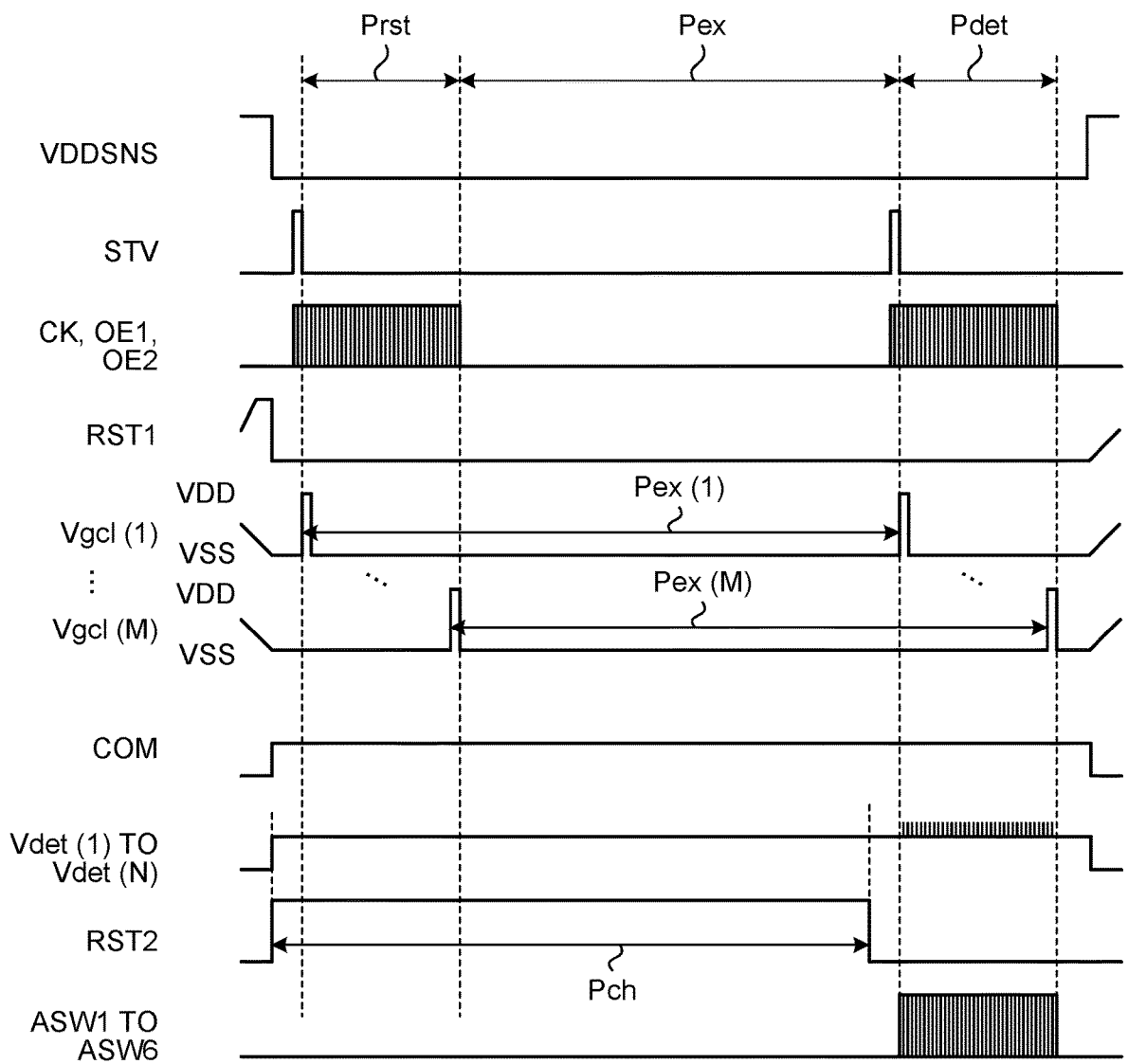
FIG. 7 is a timing waveform diagram illustrating an operation example of the detection device.
Figure 8:
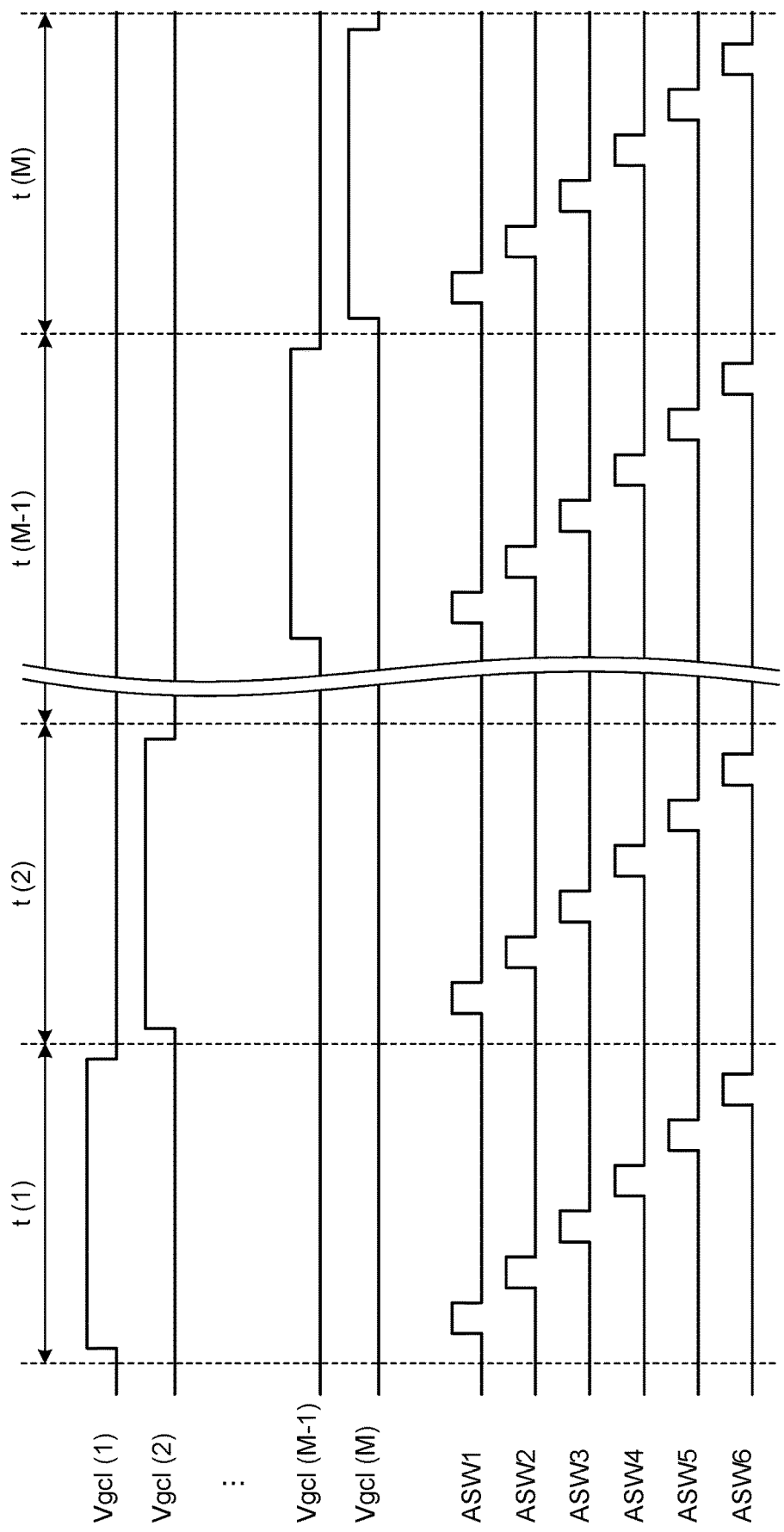
FIG. 8 is a timing waveform diagram illustrating the operation example during a reading period in FIG. 7.

The following describes an operation example of the detection device 1. FIG. 7 is a timing waveform diagram illustrating the operation example of the detection device. FIG. 8 is a timing waveform diagram illustrating the operation example during the reading period in FIG. 7.

As illustrated in FIG. 7, the detection device 1 has the reset period Prst, an exposure period Pex, and the reading period Pdet. The power supply circuit 123 supplies the sensor power supply signal VDDSNS to the anode of the photodiode PD over the reset period Prst, the exposure period Pex, and the reading period Pdet. The sensor power supply signal VDDSNS is a signal for applying a reverse bias between the anode and the cathode of the photodiode PD. For example, the reference signal COM of substantially 0.75 V is applied to the cathode of the photodiode PD, and the sensor power supply signal VDDSNS of substantially −1.25 V is applied to the anode of the photodiode PD. As a result, a reverse bias of substantially 2.0 V is applied between the anode and the cathode. At the time of detection of a wavelength of 850 nm, the reverse bias of 2 V is applied to the photodiode PD so as to obtain a high sensitivity of 0.5 A/W to 0.7 A/W, preferably approximately 0.57 A/W. The following characteristics of the photodiode PD is used: the dark current density is $1.0 \times 10^{-7}$ $A/cm^2$ when the reverse bias of 2 V is applied, and the photocurrent density is $1.2 \times 10^{-3}$ $A/cm^2$ when light having an output of substantially 2.9 $mW/cm^2$ and the wavelength of 850 nm is detected. The external quantum efficiency (EQE) is approximately 1.0 when the reverse bias of 2 V is applied when the photodiode is irradiated with the light having the wavelength of 850 nm. The control circuit 122 sets the reset signal RST2 to "H", and then, supplies the start signal STV and the clock signal CK to the gate line drive circuit 15 to start the reset period Prst. During the reset period Prst, the control circuit 122 supplies the reference signal COM to the reset circuit 17 and uses the reset signal RST2 to turn on the fourth switching elements TrR for supplying a reset voltage. This operation supplies the reference signal COM as the reset voltage to the signal lines SGL. The reference signal COM is set to, for example, 0.75 V.

During the reset period Prst, the gate line drive circuit 15 sequentially selects each of the gate lines GCL based on the start signal STV, the clock signal CK, and the reset signal RST1. The gate line drive circuit 15 sequentially supplies the gate drive signals Vgcl to each of the gate lines GCL. The gate drive signal Vgcl has a pulsed waveform having a power supply voltage VDD serving as a high-level voltage and a power supply voltage VSS serving as a low-level voltage. In FIG. 7, M gate lines GCL (where M is, for example, 256) are provided, and gate drive signals Vgcl(1) . . . , Vgcl(M) are sequentially supplied to the respective gate lines GCL.

Thus, during the reset period Prst, the capacitive elements Ca of all the partial detection areas PAA are sequentially electrically coupled to the signal lines SGL, and are supplied with the reference signal COM. As a result, the electrical charges stored in the capacitance of the capacitive elements Ca are reset.

After the gate drive signal Vgcl(M) is supplied to the gate line GCL, the exposure period Pex starts. The start timing and end timing of actual exposure periods Pex(1), Pex(M) in the partial detection areas PAA corresponding to the gate lines GCL differ from one another. Each of the exposure periods Pex(1), Pex(M) starts at a timing when the gate drive signal Vgcl changes from the power supply voltage VDD as the high-level voltage to the power supply voltage VSS as the low-level voltage during the reset period Prst. Each of the exposure periods Pex(1), Pex(M) ends at a timing when the gate drive signal Vgcl changes from the power supply voltage VSS to the power supply voltage VDD during the reading period Pdet. The lengths of exposure time of the exposure periods Pex(1), Pex(M) are equal to one another.

During the exposure period Pex, the current corresponding to the light irradiating the photodiode PD flows in each of the partial detection areas PAA. As a result, the electrical charge is stored in each of the capacitive elements Ca.

At a timing before the reading period Pdet starts, the control circuit 122 sets the reset signal RST2 to a low-level voltage. This operation stops the reset circuit 17 from operating. During the reading period Pdet, the gate line drive circuit 15 sequentially supplies the gate drive signals Vgcl(1) . . . , Vgcl(M) to the gate lines GCL in the same manner as during the reset period Prst.

Specifically, as illustrated in FIG. 8, the gate line drive circuit 15 supplies the gate drive signal Vgcl(1) at the high-level voltage (power supply voltage VDD) to the gate line GCL(1) during a period t(1). The control circuit 122 sequentially supplies the selection signals ASW1, . . . , ASW6 to the signal line selection circuit 16 during a period in which the gate drive signal Vgcl(1) is at the high-level voltage (power supply voltage VDD). This operation sequentially or simultaneously couples the signal lines SGL of the partial detection areas PAA selected by the gate drive signal Vgcl(1) to the detection circuit 48. As a result, the detection signal Vdet for each of the partial detection areas PAA is supplied to the detection circuit 48. A time of, for example, approximately 20 μs (substantially 20 μs) elapses from when the gate drive signal Vgcl(1) is set to the high level to when the first selection signal ASW1 starts to be supplied, and a time of, for example, approximately 60 μs (substantially 60 μs) elapses while each of the selection signals ASW1, . . . , ASW6 is supplied. Such a high-speed response can be achieved by using thin-film transistors (TFTs) made using low-temperature polysilicon (LTPS) having mobility of substantially 40 cm$^2$/Vs.

In the same manner, the gate line drive circuit 15 supplies the gate drive signals Vgcl(2), . . . , Vgcl(M−1), Vgcl(M) at the high-level voltage to gate lines GCL(2), . . . , GCL(M−1), GCL(M) during periods t(2), . . . , t(M−1), t(M), respectively. That is, the gate line drive circuit 15 supplies the gate drive signal Vgcl to the gate line GCL during each of the periods t(1), t(2), . . . , t(M−1), t(M). The signal line selection circuit 16 sequentially selects each of the signal lines SGL based on the selection signal ASW in each period in which the gate drive signal Vgcl is set to the high-level voltage. The signal line selection circuit 16 sequentially couples each of the signal lines SGL to the one detection circuit 48. Thus, the detection device 1 can output the detection signals Vdet of all the partial detection areas PAA to the detection circuit 48 during the reading period Pdet.

Although FIG. 8 illustrates the example in which the gate line drive circuit 15 selects one of the gate lines GCL in each of the periods t, the number of the gate lines GCL to be selected is not limited to this example. The gate line drive circuit 15 may simultaneously select a predetermined number (two or more) of the gate lines GCL and sequentially supply the gate drive signals Vgcl to the gate lines GCL in units of the predetermined number of the gate lines GCL. The signal line selection circuit 16 may also simultaneously couple a predetermined number (two or more) of the signal lines SGL to the one detection circuit 48. Moreover, the gate line drive circuit 15 may drop some gate lines GCL from all the gate lines GCL and scan the remaining. The dynamic range is, for example, approximately $10^3$ when the exposure period Pex is approximately 4.3 ms. A high resolution can be achieved by setting the frame rate to approximately 4.4 fps (substantially 4.4 fps).

Figure 9:
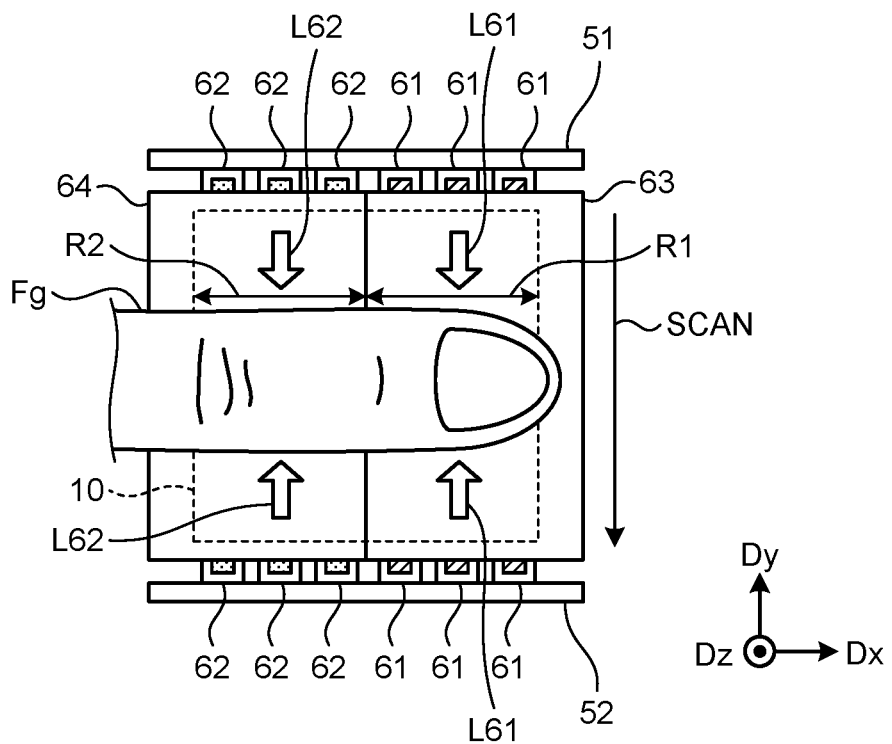
FIG. 9 is a plan view schematically illustrating a relation between the sensor, first light sources, and second light sources in the detection device according to the first embodiment.
Figure 10:
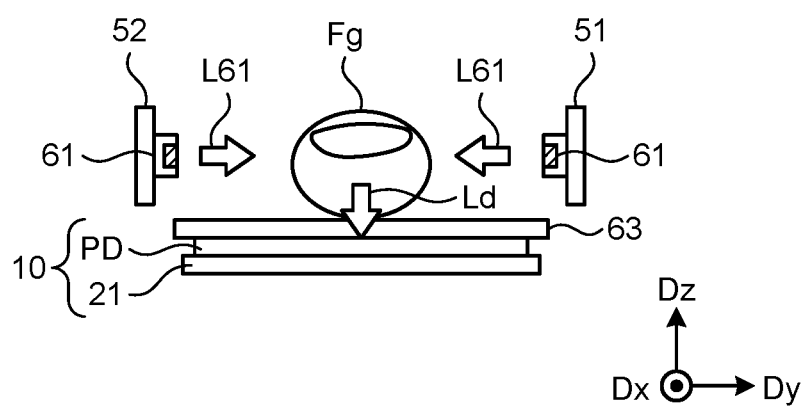
FIG. 10 is a side view schematically illustrating the relation between the sensor, the first light sources, and the second light sources of the detection device according to the first embodiment.
Figure 11:
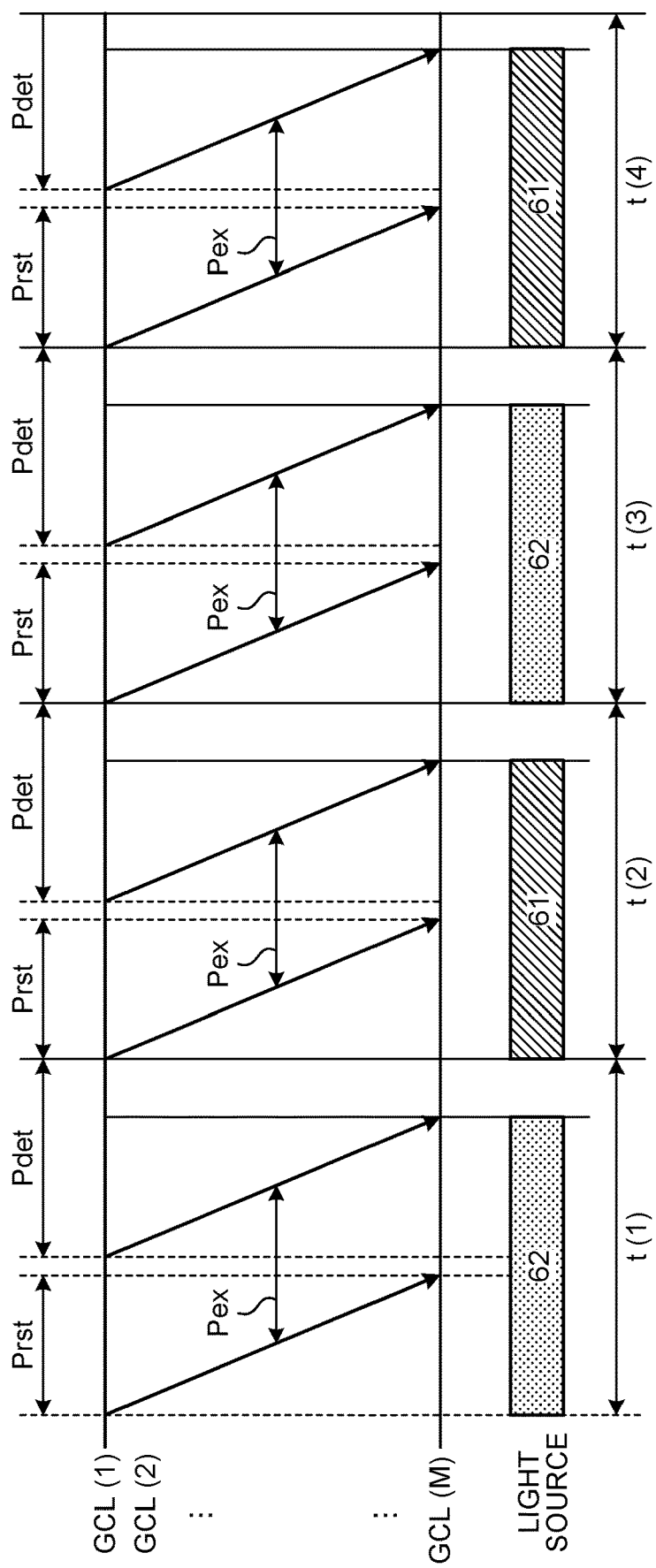
FIG. 11 is an explanatory diagram for explaining a relation between driving of the sensor and lighting operations of the light sources in the detection device.

The following describes a specific example of arrangement of the sensor 10, the first light sources 61, and the second light sources 62, and an operation example of the sensor 10, the first light sources 61, and the second light sources 62. FIG. 9 is a plan view schematically illustrating a relation between the sensor, the first light sources, and the second light sources in the detection device according to the first embodiment. FIG. 10 is a side view schematically illustrating the relation between the sensor, the first light sources, and the second light sources of the detection device according to the first embodiment. FIG. 11 is an explanatory diagram for explaining a relation between driving of the sensor and lighting operations of the light sources in the detection device.

As illustrated in FIG. 9, the sensor 10 has a first detection area R1 and a second detection area R2 adjacent to each other in the first direction Dx. The detection device 1 includes a first filter 63 and a second filter 64. The first filter 63 is disposed so as to overlap the first detection area R1 and covers both ends in the second direction Dy and one end in the first direction Dx of the sensor 10. The first filter 63 has a first transmission band including at least the first maximum emission wavelength MW1. That is, the first filter 63 has a transmission band that transmits the first light L61 emitted from the first light sources 61 and does not transmit the second light L62 emitted from the second light sources 62.

Figure 28:
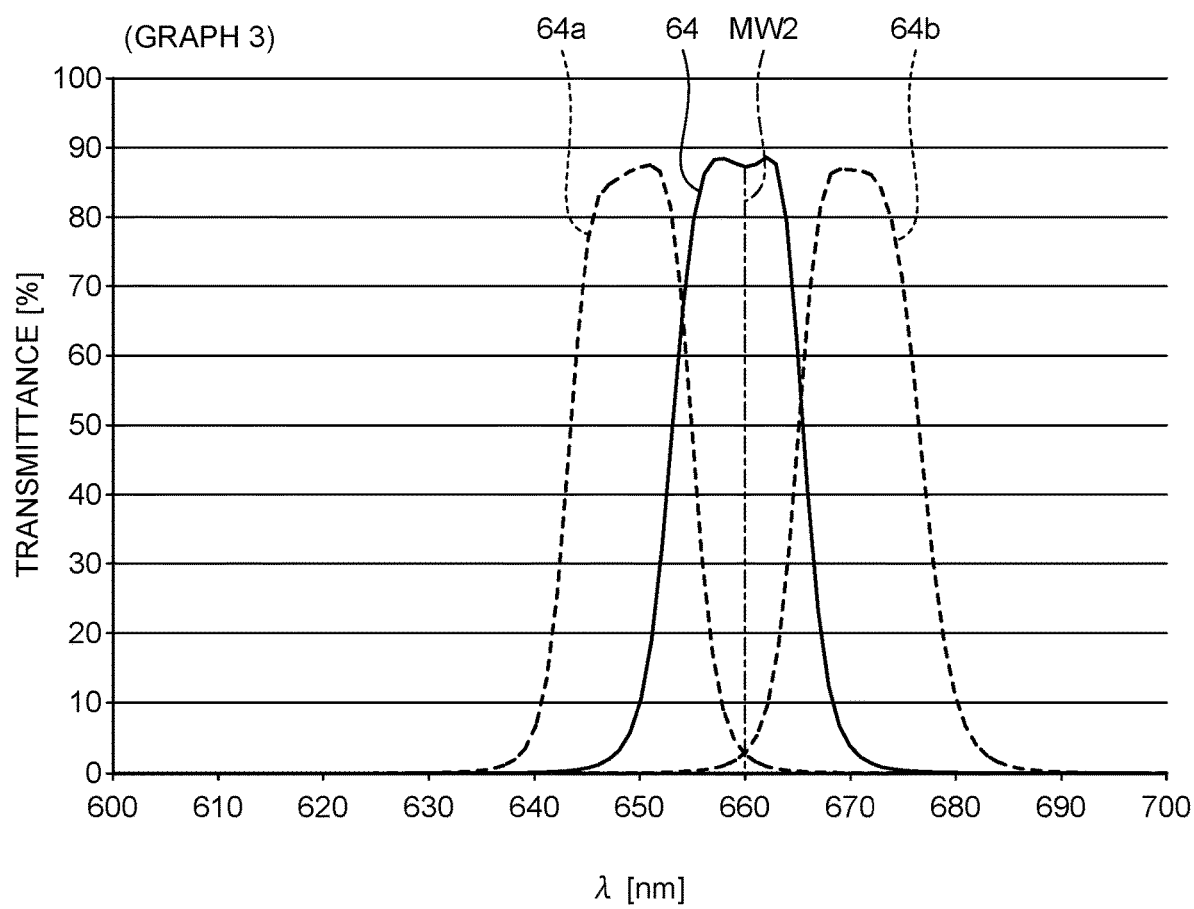
FIG. 28 is a graph illustrating examples of transmission characteristics of a second filter.

The second filter 64 is disposed so as to overlap the second detection area R2 and covers both ends in the second direction Dy and the other end in the first direction Dx of the sensor 10. FIG. 28 is a graph illustrating examples of transmission characteristics of the second filter. In Graph 3 illustrated in FIG. 28, the horizontal axis represents the wavelength, and the vertical axis represents the light transmittance. As illustrated in FIG. 28, the second filter 64 has a second transmission band including at least the second maximum emission wavelength MW2. That is, the second filter 64 has a transmission band that transmits the second light L62 emitted from the second light sources 62 and does not transmit the first light L61 emitted from the first light sources 61. Each of the first filter 63 and the second filter 64 is a band-pass filter. In the transmission characteristics of the second filter 64, the central wavelength and the half width may be changed as appropriate in accordance with the emission spectrum and the second maximum emission wavelength MW2 of the second light L62. As illustrated in FIG. 28, a second filter 64a, for example, has the central wavelength of the second transmission band at approximately 650 nm, and a second filter 64b has the central wavelength of the second transmission band at approximately 670 nm. Although not illustrated in FIG. 28, the transmission characteristics of the first filter 63 have the same waveform as that of FIG. 28 and have the central wavelength near the first maximum emission wavelength MW1.

The first filter 63 and the second filter 64 overlap the sensor 10 from one end to the other end thereof in a scan direction SCAN and are adjacent to each other in a direction (first direction Dx) intersecting the scan direction SCAN. The scan direction SCAN is a direction in which the gate line drive circuit 15 scans the gate lines GCL. That is, each of the gate lines GCL is provided across the first detection area R1 and the second detection area R2 and is coupled to corresponding ones of the partial detection areas PAA provided in the first detection area R1 and the second detection area R2. Each of the signal lines SGL is provided in one of the first detection area R1 and the second detection area R2 and is coupled to the photodiodes PD in the first detection area R1 or the photodiodes PD in the second detection area R2.

The first light source base 51 faces the second light source base 52 in the second direction Dy with the sensor 10 interposed therebetween in the plan view. A surface of the first light source base 51 facing the second light source base 52 is provided with the first light sources 61 and the second light sources 62. A surface of the second light source base 52 facing the first light source base 51 is provided with the first light sources 61 and the second light sources 62. Each of the first light source base 51 and the second light source base 52 may be provided with one first light sources 61 and more than one second light source 62.

The first light sources 61 and the second light sources 62 are arranged in the first direction Dx along the outer circumference of the detection area AA (the first detection area R1 and the second detection area R2). The first light sources 61 are provided in positions corresponding to the first detection area R1 and emit the first light L61 in a direction parallel to the second direction Dy. The first light sources 61 face one another in the second direction Dy with the first detection area R1 interposed therebetween.

The second light sources 62 are provided in positions corresponding to the second detection area R2 and emit the second light L62 in the direction parallel to the second direction Dy. The second light sources 62 face one another in the second direction Dy with the second detection area R2 interposed therebetween.

In other words, the first detection area R1 is an area provided with the first filter 63 and is an area in which the first light L61 emitted from the first light sources 61 can be detected. The second detection area R2 is an area provided with the second filter 64 and is an area in which the second light L62 emitted from the second light sources 62 can be detected.

FIG. 10 is a side view obtained by viewing the detection device 1 from the first direction Dx. As illustrated in FIG. 10, the detection target object such as the finger Fg comes into contact with or in proximity to the top of the sensor 10 with at least one of the first filter 63 and the second filter 64 (FIG. 10 does not illustrate the second filter 64) therebetween. The first light sources 61 and the second light sources 62 (FIG. 10 does not illustrate the second light sources 62) are disposed above the sensor 10 and the first filter 63 and are arranged so as to interpose the detection target object such as the finger Fg therebetween in the second direction Dy.

The first light L61 emitted from the first light sources 61 travels in the direction parallel to the second direction Dy and is incident on the finger Fg. The first light L61 is reflected on the surface of or inside the finger Fg. Part of the reflected light Ld reflected by the finger Fg travels in the third direction Dz and is transmitted through the first filter 63 to enter the first detection area R1 of the sensor 10. The first light L61 and the reflected light Ld are not transmitted through the second filter 64, and therefore are not incident on the second detection area R2.

Although not illustrated in FIG. 10, the second light L62 emitted from the second light sources 62 is also reflected on the surface of or inside the finger Fg in the same manner as the first light L61. Part of the reflected light Ld travels in the third direction Dz and is transmitted through the second filter 64 to enter the second detection area R2 of the sensor 10. The second light L62 and the reflected light Ld are not transmitted through the first filter 63, and therefore do not enter the first detection area R1. Thus, the detection signal Vdet based on the first light L61 (hereinafter, may be called "first detection signal") can be restrained from being superimposed on the detection signal Vdet based on the second light L62 (hereinafter, may be called "second detection signal").

As illustrated in FIG. 11, in each of the periods t(1) to t(4), the detection device 1 performs the processing in the reset period Prst, the exposure period Pex, and the reading period Pdet described above. During the reset period Prst and the reading period Pdet, the gate line drive circuit 15 sequentially performs scanning from the gate lines GCL(1) to GCL(M).

During the period t(1), the second light sources 62 are on, and the first light sources 61 are off. Thus, the detection device 1 performs the detection in the second detection area R2 based on the second light L62 emitted from the second light sources 62. That is, currents flow from the photodiodes PD belonging to the second detection area R2 through the signal lines SGL to the detection circuit 48. During the period t(2), the first light sources 61 are on, and the second light sources 62 are off. Thus, the detection device 1 performs the detection in the first detection area R1 based on the first light L61 emitted from the first light sources 61. That is, currents flow from the photodiodes PD belonging to the first detection area R1 through the signal lines SGL to the detection circuit 48. In the same manner, during the period t(3), the second light sources 62 are on, and the first light sources 61 are off; and during the period t(4), the first light sources 61 are on, and the second light sources 62 are off.

In this manner, the first light sources 61 and the second light sources 62 are caused to be on in a time-division manner at intervals of the period t. This operation outputs the first detection signals detected by the photodiodes PD based on the first light L61 and the second detection signals detected by the photodiodes PD based on the second light L62 to the detection circuit 48 in a time-division manner. Consequently, the first detection signals and the second detection signals are restrained from being output to the detection circuit 48 in a mutually superimposed manner. As a result, the detection device 1 can well detect the various types of the biological information.

The driving method of the first light sources 61 and the second light sources 62 can be changed as appropriate. For example, in FIG. 11, the first light sources 61 and the second light sources 62 are alternately caused to be on at intervals of the period t. However, the driving method is not limited thereto. The first light sources 61 may be turned on in successive periods t, and then, the second light sources 62 may be turned on in successive periods t.

First Modification of First Embodiment

Figure 12:
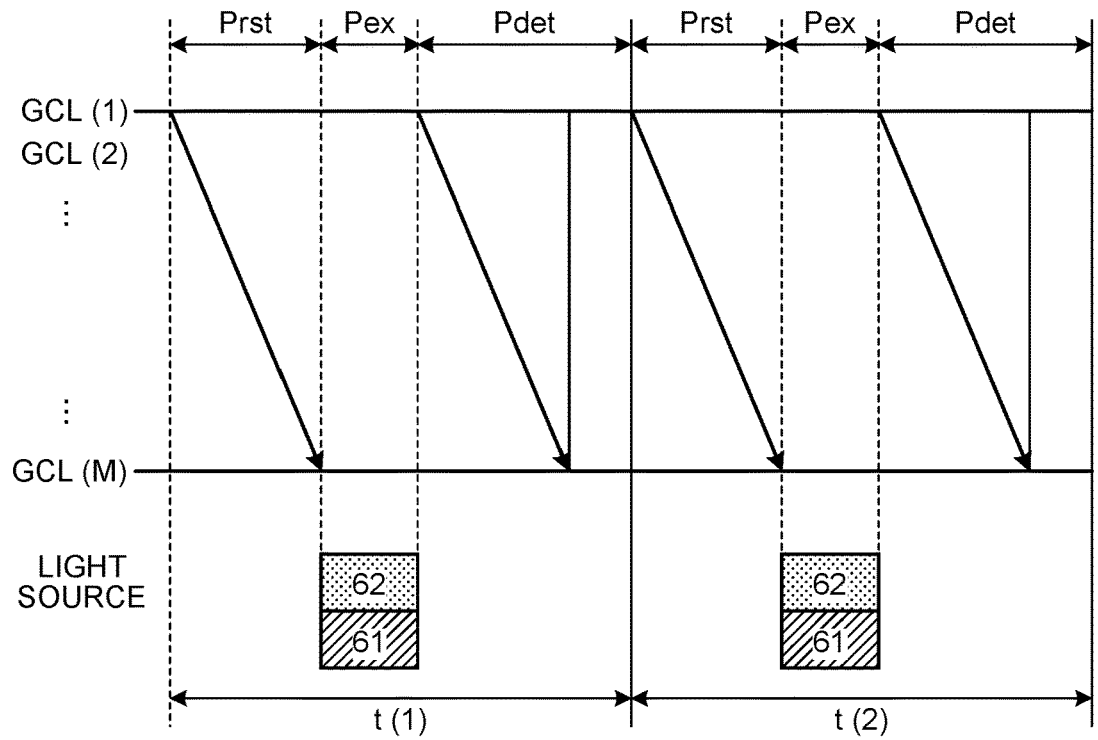
FIG. 12 is an explanatory diagram for explaining a relation between the driving of the sensor and the lighting operations of the light sources according to a first modification of the first embodiment.

FIG. 12 is an explanatory diagram for explaining a relation between the driving of the sensor and the lighting operations of the light sources according to a first modification of the first embodiment. In the first modification, the first light sources 61 and the second light sources 62 are caused to be on simultaneously. Also in this case, the first light L61 emitted from the first light sources 61 is not transmitted through the second filter 64, and therefore does not enter the second detection area R2. In the same manner, the second light L62 emitted from the second light sources 62 is not transmitted through the first filter 63, and therefore does not enter the first detection area R1. Accordingly, the first detection signals output from the first detection area R1 based on the first light L61 are restrained from being superimposed on the second detection signals output from the second detection area R2 based on the second light L62.

The first light sources 61 and the second light sources 62 are on during the exposure period Pex, and are off during the reset period Prst and the reading period Pdet. Through these operations, the detection device 1 can reduce power consumption required for the detection.

The lighting operations are not limited to the example illustrated in FIG. 12. The first light sources 61 and the second light sources 62 may be continuously on over all the periods including the reset period Prst, the exposure period Pex, and the reading period Pdet. Either of the first light sources 61 or the second light sources 62 may be on during the exposure period Pex, and the first light sources 61 and the second light sources 62 may be alternately turned on at intervals of the period t.

Second Modification of First Embodiment

Figure 13:
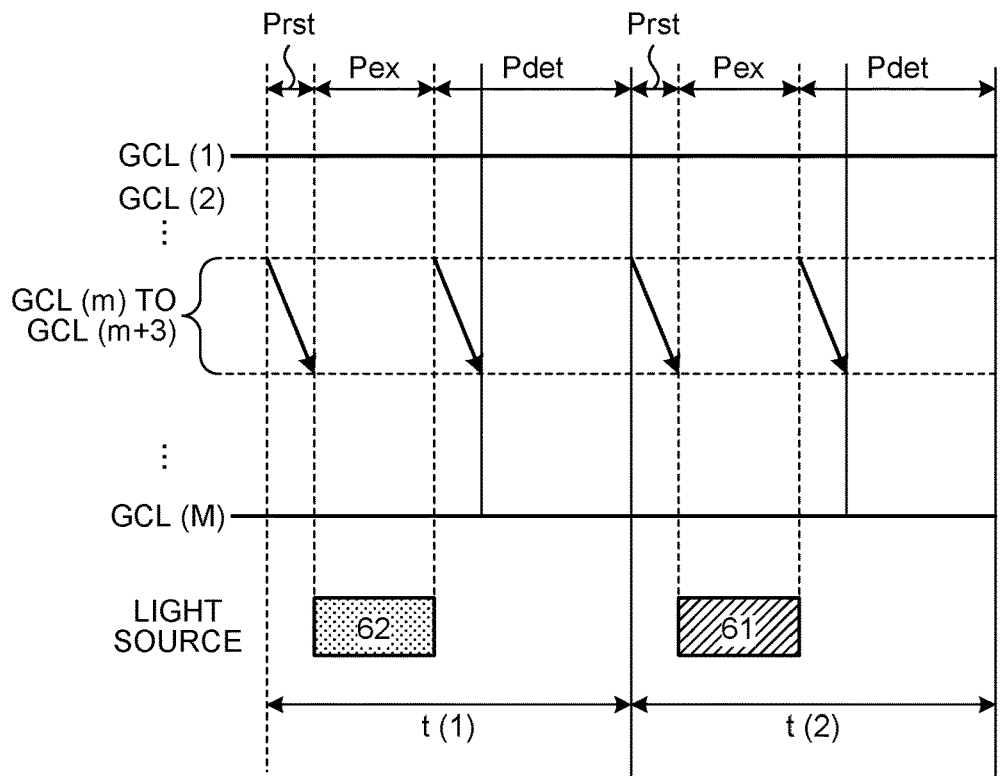
FIG. 13 is an explanatory diagram for explaining a relation between the driving of the sensor and the lighting operations of the light sources according to a second modification of the first embodiment.

FIG. 13 is an explanatory diagram for explaining a relation between the driving of the sensor and the lighting operations of the light sources according to a second modification of the first embodiment. As illustrated in FIG. 13, in the second modification, the gate line drive circuit 15 supplies the gate drive signals Vgcl to some gate lines GCL among the gate lines GCL. For example, during the reset period Prst and the reading period Pdet, the gate line drive circuit 15 sequentially supplies the gate drive signals Vgcl to four gate lines GCL(m) to GCL(m+3). The gate lines GCL(1) to GCL(m−1) and the gate lines GCL(m+4) to GCL(M) are not selected as gate lines to be driven and are not supplied with the gate drive signals Vgcl.

As a result, the first detection signals and the second detection signals are output from the partial detection areas PAA coupled to the gate lines GCL(m) to GCL(m+3). No detection signals are output from the partial detection areas PAA coupled to the gate lines GCL that are not selected.

In the present embodiment, only some of the gate lines GCL are scanned, so that the time required for the detection can be reduced. As a result, the detection is quickly performed, so that a change in the detection target object with time, such as pulsation, can be well detected. An area overlapping the finger Fg can be selected and detected, and the detection of the area overlapping the finger Fg can be repeatedly performed. As a result, the detection device 1 can increase the S/N ratio in the detection.

Any method may be used to select the gate lines GCL to be driven. For example, the gate line drive circuit 15 scans the gate lines GCL(1) to GCL(M) to perform the detection in the entire detection area AA, and the detector 40 identifies a presence and a position of the finger Fg. The control circuit 122 may select the gate lines GCL to be driven based on the position of the finger Fg. Alternatively, a capacitive touch panel may be provided, and the touch panel may identify the position of the finger Fg.

In FIG. 13, either the first light sources 61 or the second light sources 62 are on only during the exposure period Pex, and the first light sources 61 and the second light sources 62 are alternately tuned on at intervals of the period t. However, the lighting operations are not limited thereto. The first light sources 61 and the second light sources 62 may be caused to be on simultaneously, or the first light sources 61 and the second light sources 62 may be continuously on over all the periods including the reset period Prst, the exposure period Pex, and the reading period Pdet.

Second Embodiment

Figure 14:
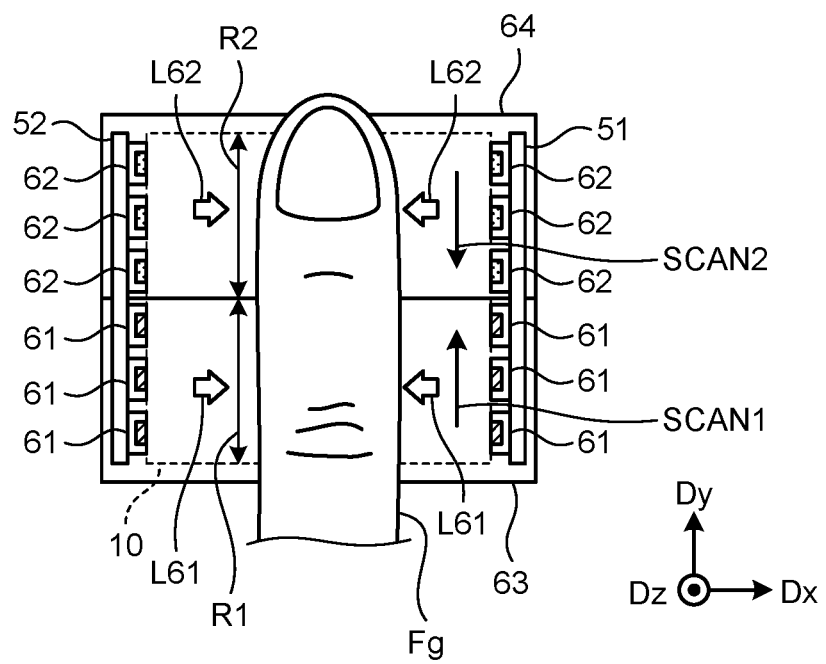
FIG. 14 is a plan view schematically illustrating a relation between the sensor, the first light sources, and the second light sources of the detection device according to a second embodiment.
Figure 15:
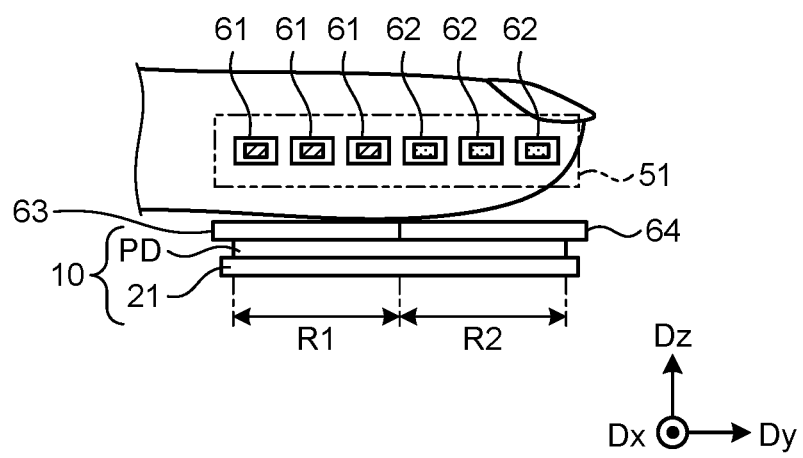
FIG. 15 is a side view schematically illustrating the relation between the sensor, the first light sources, and the second light sources of the detection device according to the second embodiment.
Figure 16:
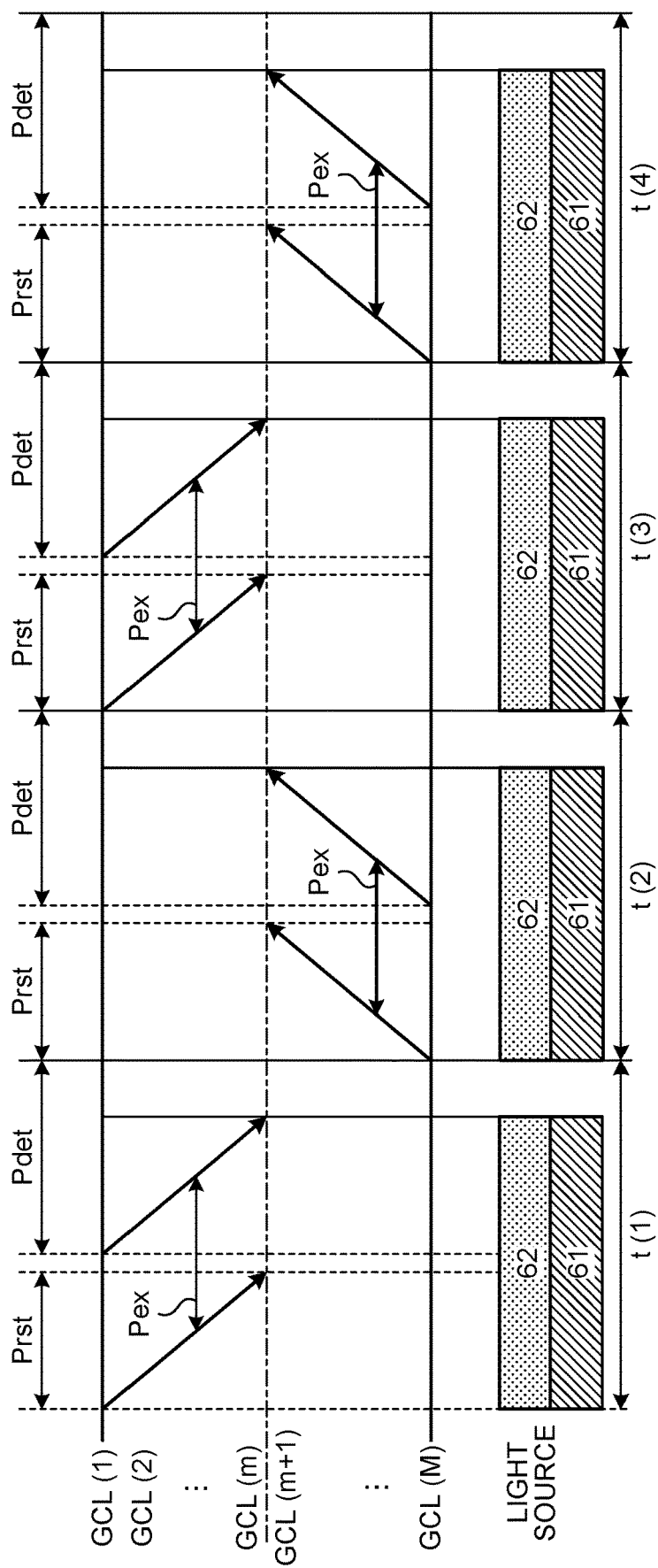
FIG. 16 is an explanatory diagram for explaining a relation between the driving of the sensor and the lighting operations of the light sources in the detection device according to the second embodiment.

FIG. 14 is a plan view schematically illustrating a relation between the sensor, the first light sources, and the second light sources of the detection device according to a second embodiment. FIG. 15 is a side view schematically illustrating the relation between the sensor, the first light sources, and the second light sources of the detection device according to the second embodiment. FIG. 16 is an explanatory diagram for explaining a relation between the driving of the sensor and the lighting operations of the light sources in the detection device according to the second embodiment. In the following description, the components described in the above-described embodiment will be denoted by the same reference numerals and will not be described.

As illustrated in FIG. 14, the first detection area R1 and the second detection area R2 of the sensor 10 arranged adjacent to each other in the second direction Dy. The first filter 63 is disposed so as to overlap the first detection area R1 and covers both ends in the first direction Dx and one end in the second direction Dy of the sensor 10. The second filter 64 is disposed so as to overlap the second detection area R2 and covers both ends in the first direction Dx and the other end in the second direction Dy of the sensor 10.

The first filter 63 and the second filter 64 overlap the sensor 10 from one end to the other end thereof in the first direction Dx, and are adjacent to each other in the second direction Dy. That is, each of the gate lines GCL is provided in either the first detection area R1 or the second detection area R2 and is coupled to corresponding ones of the partial detection areas PAA in the first detection area R1 or corresponding ones of the partial detection areas PAA in the second detection area R2. Each of the signal lines SGL is provided across the first detection area R1 and the second detection area R2 and is coupled to corresponding ones of the photodiodes PD in the first detection area R1 and corresponding ones of the photodiodes PD in the second detection area R2.

The first light source base 51 faces the second light source base 52 in the first direction Dx with the sensor 10 interposed therebetween in the plan view. A surface of the first light source base 51 facing the second light source base 52 is provided with the first light sources 61 and the second light sources 62. A surface of the second light source base 52 facing the first light source base 51 is provided with the first light sources 61 and the second light sources 62.

The first light sources 61 and the second light sources 62 are arranged in the second direction Dy along the outer circumference of the detection area AA (the first detection area R1 and the second detection area R2). The first light sources 61 are provided in positions corresponding to the first detection area R1 and emit the first light L61 in a direction parallel to the first direction Dx. The first light sources 61 face one another in the first direction Dx with the first detection area R1 interposed therebetween.

The second light sources 62 are provided in positions corresponding to the second detection area R2 and emit the second light L62 in the direction parallel to the first direction Dx. The second light sources 62 face one another in the first direction Dx with the second detection area R2 interposed therebetween.

FIG. 15 is a side view obtained by viewing the detection device 1 from the first direction Dx. As illustrated in FIG. 15, the detection target object such as the finger Fg is located above the sensor 10 with at least one of the first filter 63 and the second filter 64 interposed therebetween. The first light sources 61 and the second light sources 62 are disposed above the sensor 10, the first filter 63, and the second filter 64, and are arranged so as to interpose the detection target object such as the finger Fg therebetween in the first direction Dx.

Each of the first light L61 emitted from the first light sources 61 and the second light L62 emitted from the second light sources 62 travels in the direction parallel to the first direction Dx and is incident on the finger Fg. The first light L61 and the second light L62 are reflected and scattered on the surface of or inside the finger Fg, and part of the reflected light Ld travels in the third direction Dz. The part of the reflected light Ld is transmitted through the first filter 63 or the second filter 64 and enters the sensor 10.

As described above, each of the signal lines SGL is provided across the first detection area R1 and the second detection area R2. Therefore, in the present embodiment, the detection in the first detection area R1 and the detection in the second detection area R2 are performed in a time-division manner. Specifically, as illustrated in FIG. 16, the gate line drive circuit 15 sequentially scans the gate lines GCL(1) to GCL(m) during the period t(1). The gate lines GCL(1) to GCL(m) are the gate lines GCL belonging to the second detection area R2 illustrated in FIG. 14. The gate line drive circuit 15 scans the gate lines GCL in a second scan direction SCAN2 illustrated in FIG. 14.

The gate drive signals Vgcl are not supplied to the gate lines GCL belonging to the first detection area R1 (the gate lines GCL(m+1) to (M)) during the period t(1). As a result, the photodiodes PD in the first detection area R1 are left uncoupled from the signal lines SGL.

Thus, during the period t(1), the detection device 1 performs the detection in the second detection area R2 based on the second light L62 emitted from the second light sources 62. That is, the currents flow from the photodiodes PD belonging to the second detection area R2 through the signal lines SGL to the detection circuit 48. In the period t(1), although both the first light sources 61 and the second light sources 62 are on, the first light L61 emitted from the first light sources 61 is not transmitted through the second filter 64, and therefore, does not enter the second detection area R2. Consequently, the detection device 1 can well perform the detection based on the second light L62.

Then, during the period t(2), the gate line drive circuit 15 sequentially supplies the gate drive signals Vgcl to the gate lines GCL(M) to GCL(m+1). The gate lines GCL(M) to GCL(m+1) are gate lines GCL belonging to the first detection area R1 illustrated in FIG. 14. The gate line drive circuit 15 scans the gate lines GCL in a first scan direction SCAN1 illustrated in FIG. 14. The first scan direction SCAN1 is a direction opposite to the second scan direction SCAN2.

The gate drive signals Vgcl are not supplied to the gate lines GCL belonging to the second detection area R2 (the gate lines GCL(1) to (m)) during the period t(2). As a result, the photodiodes PD in the second detection area R2 are left uncoupled from the signal lines SGL.

Thus, during the period t(2), the detection device 1 performs the detection in the first detection area R1 based on the first light L61 emitted from the first light sources 61. That is, the currents flow from the photodiodes PD belonging to the first detection area R1 through the signal lines SGL to the detection circuit 48.

During the periods t(3) and t(4), the same operations as those in the periods t(1) and t(2), respectively, are repeatedly performed. As described above, the gate line drive circuit sequentially supplies the gate drive signals Vgcl to the gate lines GCL provided in the first detection area R1 (the gate lines GCL(m+1) to (M)) among the gate lines GCL in the first scan direction SCAN1. During a period different from the detection period of the first detection area R1, the gate line drive circuit 15 sequentially supplies the gate drive signals Vgcl to the gate lines provided in the second detection area R2 (the gate lines GCL(m+1) to GCL(M)) in the second scan direction SCAN2 opposite to the first scan direction SCAN1.

With this configuration, even in the case where each of the signal lines SGL is provided across the first detection area R1 and the second detection area R2, the first detection signals output from the first detection area R1 based on the first light L61 can be restrained from being superimposed on the second detection signals output from the second detection area R2 based on the second light L62.

Although, in FIG. 16, the first light sources 61 and the second light sources 62 are continuously on over the reset period Prst, the exposure period Pex, and the reading period Pdet, the lighting operations are not limited thereto. The operations of the first light sources 61 and the second light sources 62 illustrated in the first embodiment, the first modification, and the second modification described above can also be applied to the second embodiment.

That is, the second light sources 62 may be on and the first light sources 61 may be off during the period t(1), and the first light sources 61 may be on and the second light sources 62 may be off during the period t(2). In this manner, the first light sources 61 and the second light sources 62 may be alternately turned on. Alternatively, the first light sources 61 and the second light sources 62 may be on only during the exposure period Pex. Still alternatively, the gate line drive circuit 15 may drive some of the gate lines GCL belonging to the first detection area R1 or some of the gate lines GCL belonging to the second detection area R2 based on the position of the finger Fg.

Third Embodiment

Figure 17:
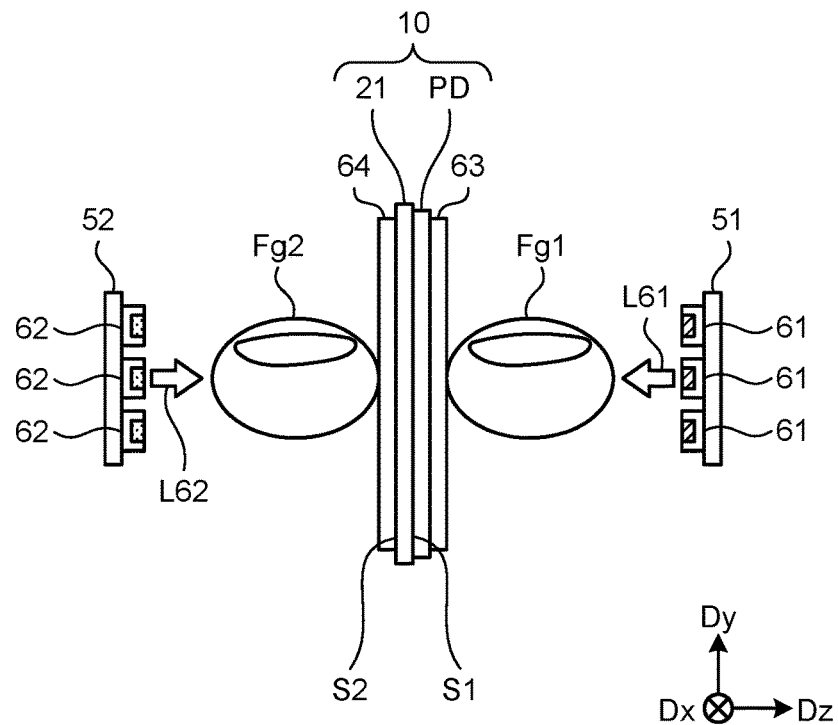
FIG. 17 is a side view schematically illustrating a relation between the sensor, the first light sources, and the second light sources of the detection device according to a third embodiment.

FIG. 17 is a side view schematically illustrating a relation between the sensor, the first light sources, and the second light sources of the detection device according to a third embodiment. As illustrated in FIG. 17, the first filter 63 is provided on the first surface S1 side of the sensor base 21. The photodiodes PD are provided between the first filter 63 and the first surface S1. The second filter 64 is provided on the second surface S2 side of the sensor base 21. That is, the sensor 10 is provided between the first filter 63 and the second filter 64 in the third direction Dz.

The first light source base 51 faces the second light source base 52 in the third direction Dz with the sensor 10 interposed therebetween. The first light source base 51 faces the first surface S1 of the sensor base 21. The first light sources 61 are provided on a surface of the first light source base 51 facing the first surface S1. That is, the first light sources 61 are provided so as to face the first surface S1 in a direction orthogonal to the first surface S1. The first filter 63 is provided between the photodiodes PD and the first light sources 61 in the direction orthogonal to the first surface S1.

The second light source base 52 faces the second surface S2 of the sensor base 21. The second light sources 62 are provided on a surface of the second light source base 52 facing the second surface S2. That is, the second light sources 62 are provided so as to face the second surface S2 in a direction orthogonal to the second surface S2. The second filter 64 is provided between the second surface S2 and the second light sources 62 in the direction orthogonal to the second surface S2.

In the third embodiment, the sensor 10 can detect the biological information in a state of being interposed between two fingers Fg1 and Fg2. The first light L61 emitted from the first light sources 61 is transmitted through the finger Fg1 and the first filter 63, and enters the sensor 10. The second light L62 emitted from the second light sources 62 is transmitted through the finger Fg2, the second filter 64, and the sensor base 21, and enters the sensor 10.

With the above-described configuration, in the third embodiment, the various types of the biological information on the fingers Fg can be detected. The driving method of the detection device 1 according to the third embodiment is the same as that of FIG. 11, and therefore, is not described in detail.

Fourth Embodiment

Figure 18:
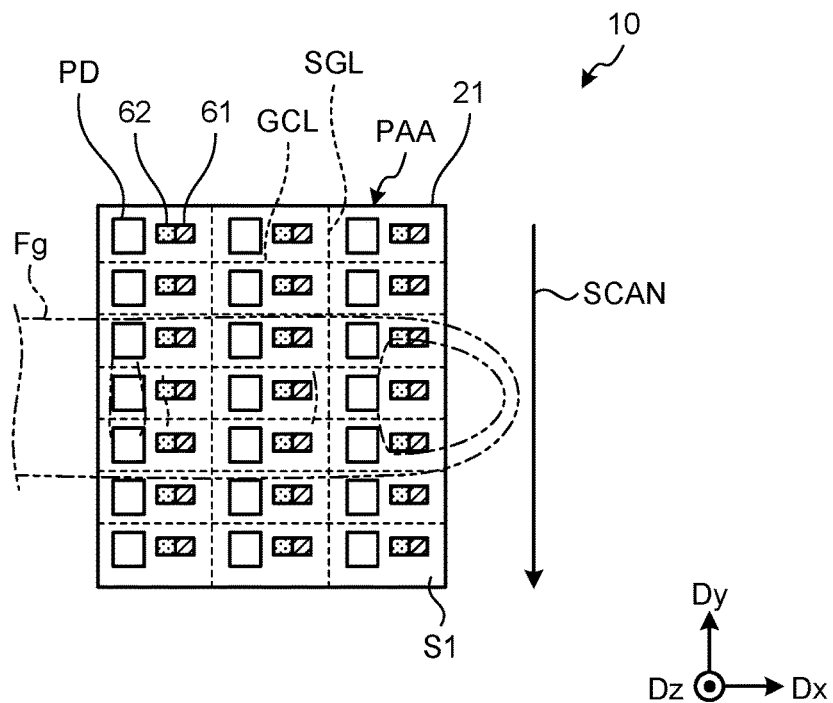
FIG. 18 is a plan view schematically illustrating a relation between the sensor, the first light sources, and the second light sources of the detection device according to a fourth embodiment.

FIG. 18 is a plan view schematically illustrating a relation between the sensor, the first light sources, and the second light sources of the detection device according to a fourth embodiment. In the fourth embodiment, the first light sources 61 and the second light sources 62 are provided on the first surface S1 of the sensor base 21, as illustrated in FIG. 18

Specifically, the first light source 61 and the second light source 62 are provided in each of the partial detection areas PAA and are disposed adjacent to the photodiode PD in an area surrounded by the signal lines SGL and the gate lines GCL.

Each of the first light L61 emitted from the first light source 61 and the second light L62 emitted from the second light source 62 travels in a direction parallel to the third direction Dz, is reflected on the surface of or inside the finger Fg, and enters the photodiode PD.

Also in the fourth embodiment, different items of the biological information can be detected using the first light L61 and the second light L62. Since the fourth embodiment does not require provision of the first light source base 51 and the second light source base 52, the detection device 1 can be reduced in size. The driving method of the detection device 1 according to the fourth embodiment is the same as that of FIG. 11, and therefore, is not described in detail. The arrangement of the first light sources 61 and the second light sources 62 illustrated in FIG. 18 is merely an example and can be changed as appropriate. For example, each of the partial detection areas PAA may be provided with either the first light source 61 or the second light source 62. In this case, the partial detection areas PAA each provided with the first light source 61 and the partial detection areas PAA each provided with the second light source 62 may be alternately arranged.

Fifth Embodiment

Figure 19:
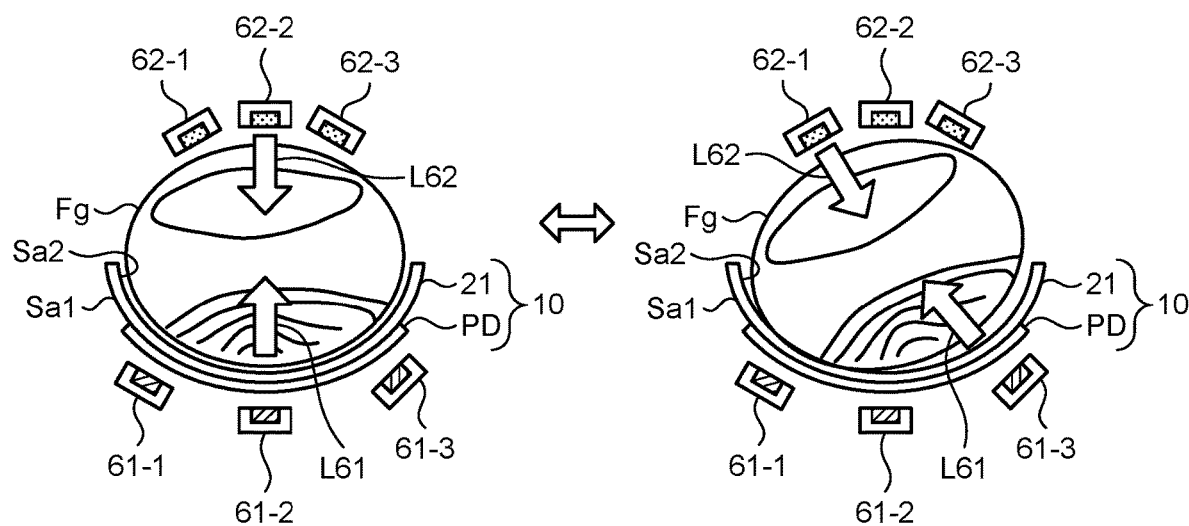
FIG. 19 depicts side views each schematically illustrating a relation between the sensor, first light sources, and second light sources of the detection device according to a fifth embodiment.

FIG. 19 depicts side views each schematically illustrating a relation between the sensor, first light sources, and second light sources of the detection device according to a fifth embodiment. FIG. 19 illustrates operation examples in the cases of different relative positional relations between the finger Fg and the sensor 10. As illustrated in FIG. 19, the sensor base 21 has a first curved surface Sa1 and a second curved surface Sa2 on the opposite side of the first curved surface Sa1. The first curved surface Sa1 is curved in a convex manner in a direction from the second curved surface Sa2 toward the first curved surface Sa1. The second curved surface Sa2 is curved in a concave manner along the surface of the finger Fg. The first curved surface Sa1 is provided with the photodiodes PD. The sensor base 21 may be made of a light-transmitting film-shaped resin material or a curved glass substrate.

A plurality of first light sources 61-1, 61-2, and 61-3 are provided along the first curved surface Sa1 and emit the first light L61 in different directions. A plurality of second light sources 62-1, 62-2, and 62-3 are provided so as to face the second curved surface Sa2 and emit the second light L62 in different directions. The first light source 61-1 and the second light source 62-3 are disposed so as to interpose the finger Fg therebetween and emit the first light L61 and the second light L62 in the opposite directions. In the same manner, the first light source 61-2 and the second light source 62-2 are disposed so as to interpose the finger Fg therebetween and emit the first light L61 and the second light L62 in the opposite directions. The first light source 61-3 and the second light source 62-1 are disposed so as to interpose the finger Fg therebetween and emit the first light L61 and the second light L62 in the opposite directions.

In the following description, the first light sources 61-1, 61-2, and 61-3 will each be referred to as the first light source 61 when they need not be distinguished from one another, and the second light sources 62-1, 62-2, and 62-3 will each be referred to as the second light source 62 when they need not be distinguished from one another.

Although not illustrated in FIG. 19, each of the first light source base 51 and the second light source base 52 has a curved shape along the surface of the finger Fg. Alternatively, one light source base may be formed into a ring shape so as to surround the finger Fg, and the first light sources 61 and the second light sources 62 may be provided on the inner circumferential surface of the light source base.

In the fifth embodiment, the first light sources 61-1, 61-2, and 61-3 are turned on, and the fingerprint of the finger Fg is detected. The control circuit 122 detects the position and orientation of the finger Fg based on the information on the fingerprint.

As illustrated in the left-hand part of FIG. 19, when the ball of the finger Fg straightly faces the bottom of the sensor 10, the control circuit 122 turns on the first light source 61-2 and the second light source 62-2 among the first light sources 61-1, 61-2, and 61-3 and the second light sources 62-1, 62-2, and 62-3. The first light L61 emitted from the first light source 61-2 is reflected on the surface of or inside the finger Fg and enters the photodiode PD. The second light L62 emitted from the second light source 62-2 is transmitted through the finger Fg and enters the photodiode PD.

The right-hand part of FIG. 19 illustrates a case where the relative positional relation between the finger Fg and the sensor 10 is different, for example, a case where the ball of the finger Fg is located so as to face a position shifted from the bottom of the sensor 10. In this case, the control circuit 122 turns on the first light source 61-3 and the second light source 62-1 among the first light sources 61-1, 61-2, and 61-3 and the second light sources 62-1, 62-2, and 62-3.

In this manner, in the fifth embodiment, even when the relative positional relation between the finger Fg and the sensor 10 is shifted, the first light source 61 and the second light source 62 corresponding to the position (rotation angle) of the finger Fg are selected from among the first light sources 61 and the second light sources 62 based on the positional information on the fingerprint of the finger Fg. As a result, the first light L61 and the second light L62 can well irradiate the finger Fg, and the biological information can be detected.

The first light sources 61-1, 61-2, and 61-3 and the second light sources 62-1, 62-2, and 62-3 are arranged in different positions and at different angles. Therefore, the detection device 1 can detect the biological information such as the blood vessel images observed from different angles by sequentially turning on the first light sources 61-1, 61-2, and 61-3 and the second light sources 62-1, 62-2, and 62-3. Then, a stereoscopic blood vessel image can be obtained by performing image processing on these blood vessel images. Through this processing, the detection device 1 can increase accuracy of personal authentication when it is used for, for example, biometrics.

Third Modification of Fifth Embodiment

Figure 20:
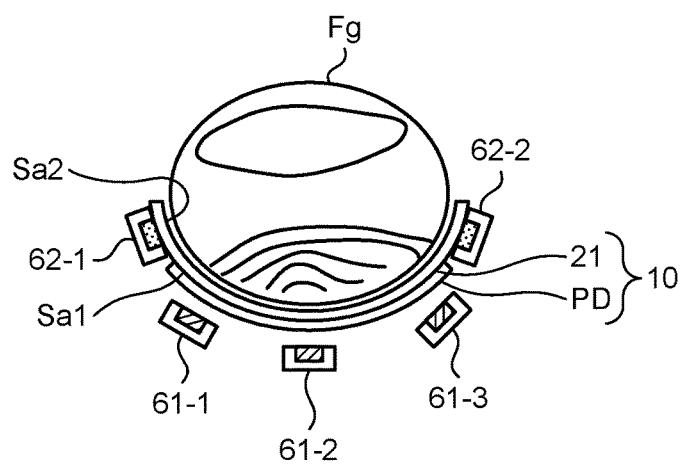
FIG. 20 is a side view schematically illustrating a relation between the sensor, the first light sources, and the second light sources of the detection device according to a third modification of the fifth embodiment.

FIG. 20 is a side view schematically illustrating a relation between the sensor, the first light sources, and the second light sources of the detection device according to a third modification of the fifth embodiment. As illustrated in FIG. 20, the third modification differs from the fifth embodiment in that the second light sources 62-1 and 62-2 are provided on the sensor base 21.

Specifically, the second light sources 62-1 and 62-2 are provided at outer edges of the first curved surface Sa1 of the sensor base 21. In other words, each of the second light sources 62-1 and 62-2 is provided between the photodiode PD and an end of the sensor base 21, and the photodiode PD is provided between the second light source 62-1 and the second light sources 62-2. The second light sources 62-1 and 62-2 are provided in positions and at angles different from those of the first light sources 61-1, 61-2, and 61-3 and can emit the second light L62 at angles different from those of the first light L61.

Also in the third modification, even when the relative positional relation between the finger Fg and the sensor 10 is shifted, the finger Fg can be irradiated with the first light L61 or the second light L62 at appropriate angle. Since the second light source base 52 can be eliminated, the configuration of the detection device 1 can be simplified.

Sixth Embodiment

Figure 21:
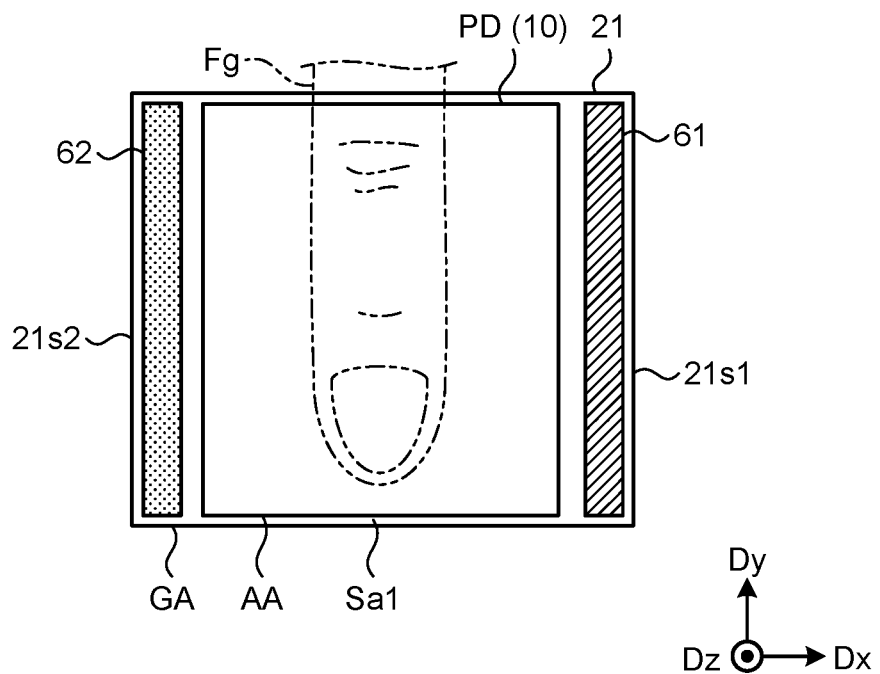
FIG. 21 is a plan view schematically illustrating a relation between the sensor, a first light source, and a second light source of the detection device according to a sixth embodiment.
Figure 22:
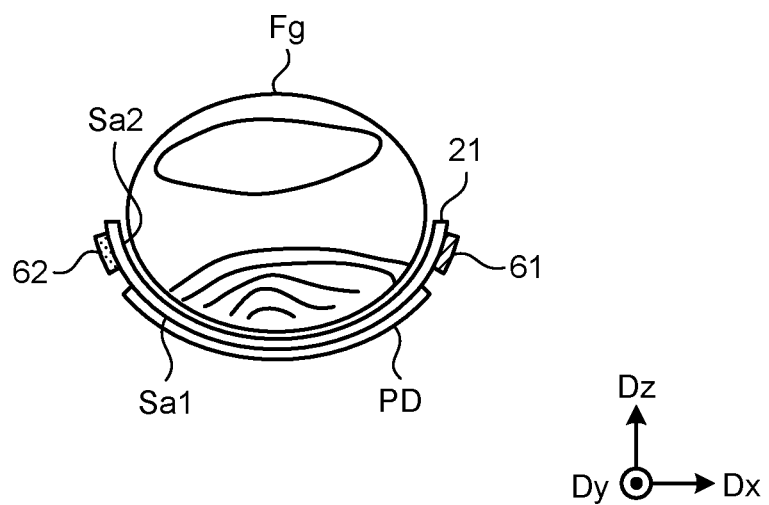
FIG. 22 is a side view schematically illustrating the relation between the sensor, the first light source, and the second light source of the detection device according to the sixth embodiment.

FIG. 21 is a plan view schematically illustrating a relation between the sensor, the first light source, and the second light source of the detection device according to a sixth embodiment. FIG. 22 is a side view schematically illustrating the relation between the sensor, the first light source, and the second light source of the detection device according to the sixth embodiment.

As illustrated in FIG. 21, the first light source 61 and the second light source 62 are provided in the peripheral area GA of the sensor base 21. Specifically, the sensor base 21 has a first side 21s1 and a second side 21s2 that face each other in the first direction Dx. The first light source 61 is provided in an area of the peripheral area GA between the first side 21s1 and the outer circumference of the sensor 10. The second light source 62 is provided in an area of the peripheral area GA between the second side 21s2 and the outer circumference of the sensor 10. The detection area AA is disposed between the first light source 61 and the second light source 62.

FIG. 21 schematically illustrates the first light source 61 and the second light source 62 as rectangular shapes. However, as described above, inorganic LEDs or organic ELs may be arranged as the first light source 61 and the second light source 62.

As illustrated in FIG. 22, the sensor base 21 has the first curved surface Sa1 and the second curved surface Sa2 in the same manner as in the fifth embodiment. The first light source 61 and the second light source 62 are provided on the first curved surface Sa1. The photodiodes PD are provided between the first light source 61 and the second light source 62. The second curved surface Sa2 has a curved shape along the surface of the ball of the finger Fg.

Each of the first light L61 emitted from the first light source 61 and the second light L62 emitted from the second light source 62 is transmitted through the sensor base 21 and is incident on the finger Fg. The first light L61 and the second light L62 are reflected on the surface of or inside the finger Fg and are transmitted through the sensor base 21 to enter the photodiodes PD.

Since the sixth embodiment does not require provision of the first light source base 51 and the second light source base 52, the detection device 1 can be reduced in size. Since the first light source 61 and the second light source 62 are provided in the peripheral area GA, the circuit configuration of the partial detection areas PAA can be simpler than that of the fourth embodiment.

Seventh Embodiment

Figure 23:
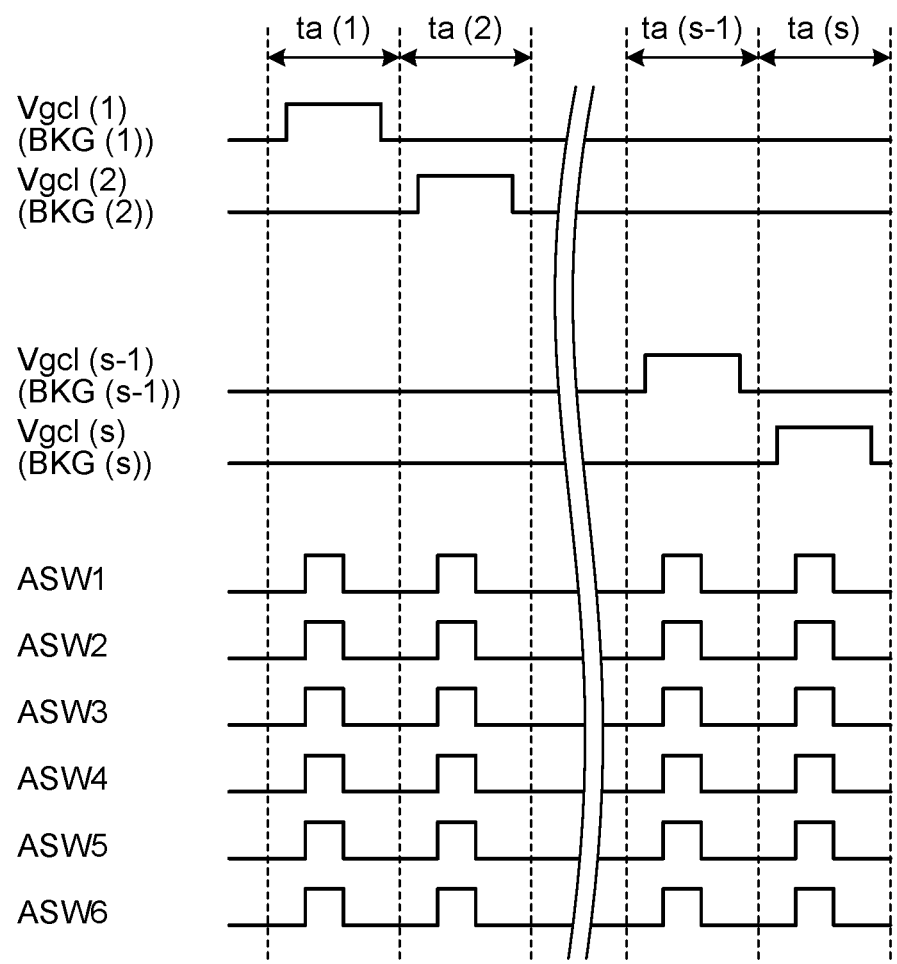
FIG. 23 is a timing waveform diagram illustrating an operation example of the detection device according to a seventh embodiment.

FIG. 23 is a timing waveform diagram illustrating an operation example of the detection device according to a seventh embodiment. In the seventh embodiment, the gate line drive circuit 15 supplies the gate drive signals Vgcl at the high-level voltage (power supply voltage VDD) to a gate line block BKG(1) including more than one of the gate lines GCL during a period ta(1). The gate line block BKG(1) includes, for example, the six gate lines GCL(1) to GCL(6) illustrated in FIG. 3. The control circuit 122 simultaneously supplies the selection signals ASW1, . . . , ASW6 to the signal line selection circuit 16 during a period in which the gate drive signals Vgcl are at the high-level voltage (power supply voltage VDD). This operation causes the signal line selection circuit 16 to simultaneously couple six of the signal lines SGL to the detection circuit 48. As a result, the detection signals Vdet of the detection area groups PAG1 and PAG2 illustrated in FIG. 3 are supplied to the detection circuit 48.

In the same manner, the gate line drive circuit 15 supplies gate drive signals Vgcl(2), . . . , Vgcl(s−1), Vgcl(s) at the high-level voltage to gate line blocks BKG(2), . . . , BKG(s−1), BKG(s) during periods ta(2), . . . , ta(s−1), ta(s), respectively. That is, the gate line drive circuit 15 simultaneously supplies the gate drive signals Vgcl to more than one of the gate lines GCL for each period ta.

Thus, the detection device 1 can output the detection signals Vdet of each of the detection area groups PAG to the detection circuit 48 during the reading period Pdet. The detection device 1 can increase the S/N ratio in the detection to a level higher than that in the case of performing the detection for each of the partial detection areas PAA. Consequently, the detection device 1 can well detect the biological information such as the blood vessel image. In the seventh embodiment, the time required for the detection in the entire area of the detection area AA can be reduced to quickly perform the detection, so that a change in the blood vessel image with time such as the pulse wave can be well detected.

Although FIG. 23 illustrates the example in which the gate line drive circuit 15 drives the six of the gate lines GCL in a bundle, the driving method is not limited to this example. The gate line drive circuit 15 may drive five or less of the gate lines GCL in a bundle, or seven or more of the gate lines GCL in a bundle. The signal line selection circuit 16 may simultaneously couple five or less of the signal lines SGL to the detection circuit 48, or seven or more of the signal lines SGL to the detection circuit 48.

The detection device 1 may have a period in which the detection is performed for each of the partial detection areas PAA and a period in which the detection is performed for each of the detection area groups PAG that are provided in a time-division manner. For example, when performing the detection, such as the fingerprint detection, at a high resolution (at a small detection pitch), the detection device 1 performs the detection for each of the partial detection areas PAA; and when performing the detection of, for example, the pulse wave that need not be detected at a high resolution, the detection device 1 performs the detection for each of the detection area groups PAG. In this case, the detection device 1 may perform the detection by switching the lighting of the first light sources 61 and the lighting of the second light sources 62 in a time-division manner between the period for detection for each of the partial detection areas PAA and the period for detection for each of the detection area groups PAG. By this operation, the detection device 1 can satisfy both the accurate detection and the detection of the temporal change according to the differences in the biological information.

Each of the detection area groups PAG1 and PAG2 illustrated in FIG. 3 includes a total of 36 (=6×6) of the partial detection areas PAA (photodiodes PD). However, the number of the partial detection areas PAA (photodiodes PD) included in each of the detection area groups PAG1 and PAG2 may be equal to or smaller than 35, or may be equal to or larger than 37. In the seventh embodiment, the number of the gate lines GCL selected by the gate line drive circuit 15 may differ from the number of the signal lines SGL selected by the signal line selection circuit 16. That is, in each of the detection area groups PAG1 and PAG2, the number of the partial detection areas PAA (photodiodes PD) arranged in the first direction Dx may differ from the number of the partial detection areas PAA (photodiodes PD) arranged in the second direction Dy.

Although FIG. 3 illustrates the two detection area groups PAG1 and PAG2 adjacent to each other in the first direction Dx, three or more of the detection area groups PAG are arranged in the first direction Dx, and more than one of the detection area groups PAG are arranged in the second direction Dy. That is, the detection area groups PAG are arranged in a matrix having a row-column configuration in the first direction Dx and the second direction Dy.

Eighth Embodiment

Figure 24:
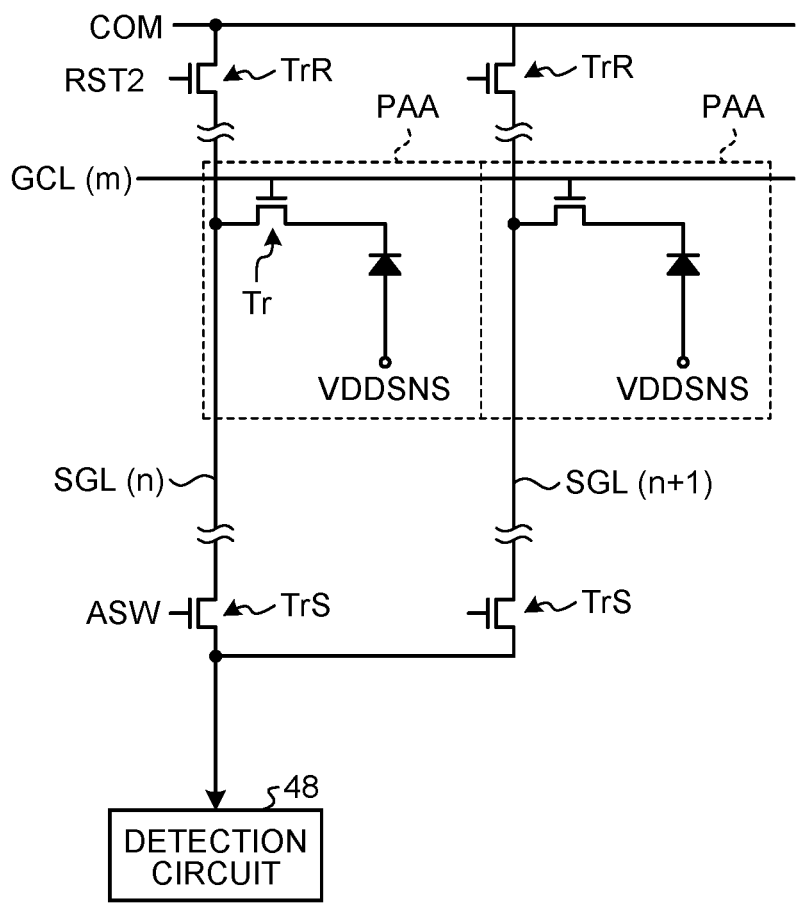
FIG. 24 is a circuit diagram illustrating the partial detection areas of the detection device according to an eighth embodiment.
Figure 25:
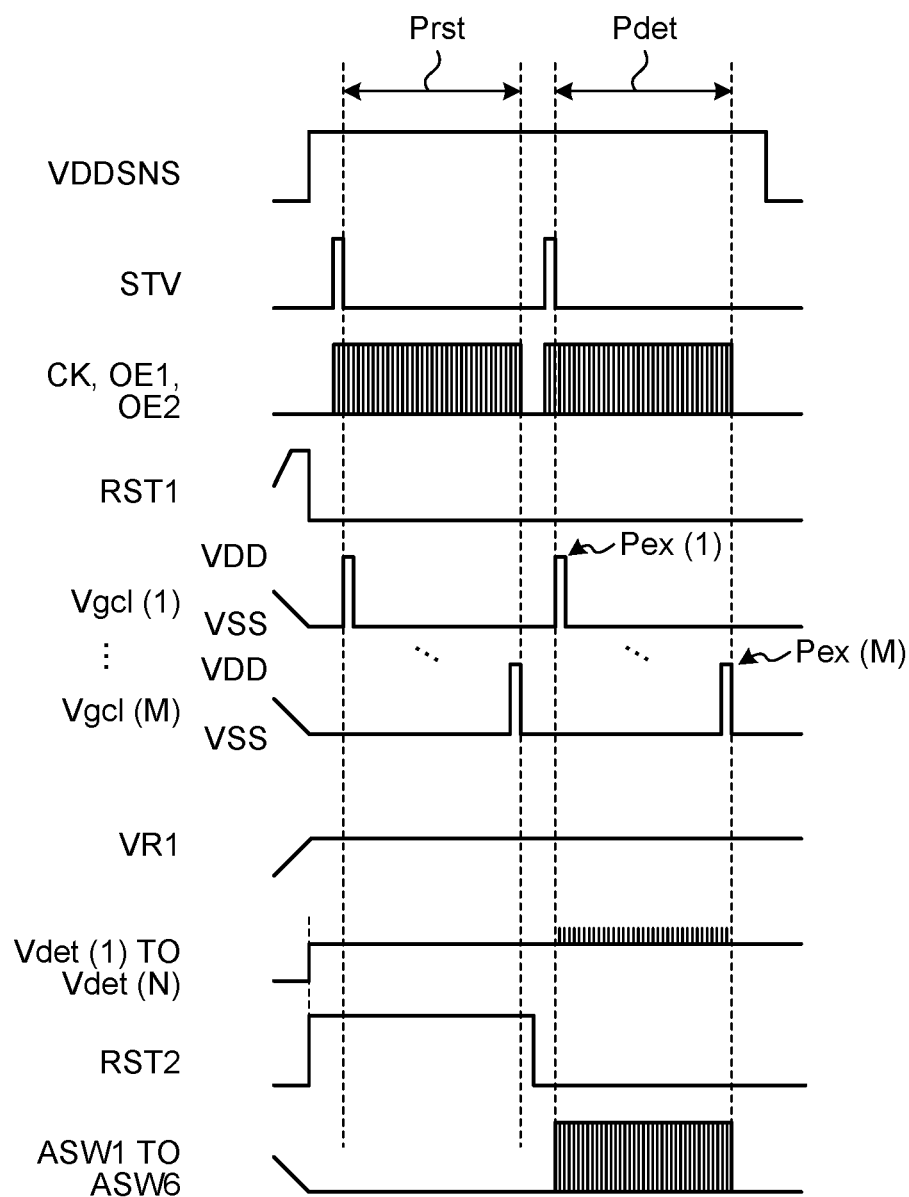
FIG. 25 is a timing waveform diagram illustrating an operation example of the detection device according to the eighth embodiment.

FIG. 24 is a circuit diagram illustrating the partial detection areas of the detection device according to an eighth embodiment. FIG. 25 is a timing waveform diagram illustrating an operation example of the detection device according to the eighth embodiment. As illustrated in FIG. 24, in the eighth embodiment, the partial detection area PAA does not include the capacitive element Ca. That is, the source of the first switching element Tr is coupled to the signal line SGL, and the drain of the first switching element Tr is coupled to the cathode of the photodiode PD.

When the partial detection area PAA is irradiated with light in the period during which the first switching element Tr is on, a current corresponding to an amount of the light flows through the photodiode PD, and the current flows from the photodiode PD through the signal line SGL to the detection circuit 48. That is, in the eighth embodiment, time for storing the electrical charge in the capacitive element Ca can be eliminated.

As illustrated in FIG. 25, after the gate drive signal Vgcl(M) is supplied to the gate line GCL(M) in the reset period Prst, the exposure period Pex is skipped and the reading period Pdet starts. During the reading period Pdet, when the gate drive signal Vgcl is sequentially supplied to each of the gate lines GCL, the first switching element Tr is turned on, and the photodiode PD is coupled to the signal line SGL. The current flows from the photodiode PD to the detection circuit 48 during the period when the first switching element Tr is on. In other words, a period Pdet during which the gate drive signal Vgcl serving as the high-level voltage signal is supplied in the reading period is the exposure period Pex.

In the eighth embodiment, the detection in the entire area of the detection area AA can be quickly performed, so that the change in the blood vessel image with time such as the pulse wave can be well detected.

In the first to the eighth embodiments, the case has been described where the gate line drive circuit 15 performs the time-division selective driving of sequentially supplying the gate drive signals Vgcl to the gate lines GCL. However, the driving method is not limited to this case. The sensor 10 may perform code division selection driving (hereinafter, called "code division multiplexing (CDM) driving") to perform the detection. Since the CDM driving and a drive circuit thereof are described in Japanese Patent Application No. 2018-005178, what is described in Japanese Patent Application No. 2018-005178 is included in the present embodiment and will not be described herein.

Although the preferred embodiments of the present disclosure have been described above, the present disclosure is not limited to the embodiments described above. The content disclosed in the embodiments is merely an example and can be variously modified within the scope not departing from the gist of the present disclosure. Any modifications appropriately made within the scope not departing from the gist of the present disclosure also naturally belong to the technical scope of the present disclosure.

What is claimed is:

1. A detection device comprising:
   a sensor base;
   a plurality of photoelectric conversion elements that are provided in a detection area of the sensor base and are configured to receive light incident thereon and output signals corresponding to the received light;
a plurality of switching elements provided in the respective photoelectric conversion elements;
a plurality of gate lines that are coupled to the switching elements and extend in a first direction;
a first light source configured to emit first light having a first maximum emission wavelength; and
a second light source configured to emit second light having a second maximum emission wavelength, wherein
the detection area has a first detection area and a second detection area adjacent to each other in a second direction intersecting the first direction,
the first light source and the second light source are arranged in the second direction along an outer circumference of the detection area,
the first light source is provided in a position corresponding to the first detection area and is configured to emit the first light in a direction parallel to the first direction,
the second light source is provided in a position corresponding to the second detection area and is configured to emit the second light in the direction parallel to the first direction, and
the detection device further comprises a gate line drive circuit configured to
sequentially supply drive signals to the gate lines provided in the first detection area in a first scan direction and
sequentially supply the drive signals to the gate lines provided in the second detection area in a second scan direction opposite to the first scan direction.

2. The detection device according to claim 1, comprising a plurality of the first light sources and a plurality of the second light sources, wherein
the first light sources face one another in the first direction with the first detection area interposed therebetween, and
the second light sources face one another in the first direction with the second detection area interposed therebetween.

3. The detection device according to claim 1, further comprising:
a first filter that is disposed so as to overlap the first detection area and has a first transmission band including at least the first maximum emission wavelength; and
a second filter that is disposed so as to overlap the second detection area and has a second transmission band including at least the second maximum emission wavelength.

4. The detection device according to claim 1, wherein
the first light is visible light, and
the second light is infrared light.

5. The detection device according to claim 1, further comprising a light source base provided with at least either the first light source or the second light source.

* * * * *